US008703797B2

(12) United States Patent
Fang et al.

(10) Patent No.: US 8,703,797 B2
(45) Date of Patent: Apr. 22, 2014

(54) CONDENSED RING PYRIDINE COMPOUNDS AS SUBTYPE-SELECTIVE MODULATORS OF SPHINGOSINE-1-PHOSPHATE-2 (S1P$_2$) RECEPTORS

(71) Applicant: Allergan, Inc., Irvine, CA (US)

(72) Inventors: Wenkui K. Fang, Irvine, CA (US); Evelyn G. Corpuz, Irvine, CA (US); Wha-Bin Im, Irvine, CA (US); Ken Chow, Newport Coast, CA (US); Liming Wang, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/929,451

(22) Filed: Jun. 27, 2013

(65) Prior Publication Data

US 2013/0296361 A1    Nov. 7, 2013

Related U.S. Application Data

(62) Division of application No. 13/498,499, filed as application No. PCT/US2010/050486 on Sep. 28, 2010, now Pat. No. 8,507,682.

(60) Provisional application No. 61/246,642, filed on Sep. 29, 2009.

(51) Int. Cl.
  *C07D 471/04* (2006.01)
  *C07D 215/38* (2006.01)

(52) U.S. Cl.
  USPC .................. 514/303; 514/300; 514/313

(58) Field of Classification Search
  None
  See application file for complete search history.

(56) References Cited

U.S. PATENT DOCUMENTS

| | | | |
|---|---|---|---|
| 4,952,683 A | 8/1990 | Tschannen et al. |
| 5,102,901 A | 4/1992 | van Wijngaarden et al. |
| 5,110,987 A | 5/1992 | Liotta et al. |
| 5,294,722 A | 3/1994 | Kim |
| 5,403,851 A | 4/1995 | D'Orlando et al. |
| 5,580,878 A | 12/1996 | D'Orlando et al. |
| 6,235,912 B1 | 5/2001 | Takesako et al. |
| 6,239,297 B1 | 5/2001 | Takesako et al. |
| 2003/0125371 A1 | 7/2003 | Elokdah et al. |

FOREIGN PATENT DOCUMENTS

| | | | |
|---|---|---|---|
| EP | 1424078 A1 | 6/2004 |
| EP | 1510516 A1 | 3/2005 |
| WO | WO01/098301 A1 | 12/2001 |
| WO | WO 01/098301 A1 | 12/2001 |
| WO | WO 02/098301 A1 | 12/2002 |
| WO | 03-080578 A1 | 10/2003 |
| WO | 2003-080578 A1 | 10/2003 |
| WO | 2008154470 | 12/2008 |
| WO | WO2008154470 | 12/2008 |
| WO | 2009-074969 A2 | 6/2009 |

OTHER PUBLICATIONS

Huwiler et al., New Players on the Center Stage: Sphingosine 1-Phosphate and Its Receptors as Drug Targets, 75(10) Biochemical Pharmacology 1893-1900 (2008).*
Athanasia Skoura, et al., Essential role of sphingosine 1—phosphate receptor 2 in pathological angiogenesis of the mouse retina, Research Article, Sep. 4, 2007, pp. 2506-2516, vol. 117, Issue 9, J Clin Invest., US.
S. Aoki, et al., The Suppressive Effect of Sphingosine 1-Phosphate on Monocyte-Endothelium Adhesion May be Mediated by the Rearrangement of the Endothelial Integrins, Journal of Thrombosis and Haemostasis, Mar. 26, 2007, 1292-1301, 5, US.
Serriere-Lanneau, et al., The sphingosine 1-phosphate receptor S1P2 triggers hepatic wound healing, Research Communication, 2007, 2005-2013, 21, The FASEB Journal, US.
Soman Mehrotra, et al., Substituted Thiosemicarbazido/Semicarbazido Quinolines As Possible Antimalarials, Journal of Heterocyclic Chemistry, Sep. 1980, 1213-1214, 17, ., US.
International Search Report for PCT/US2010/050486 Dec. 1, 2010.
Ana Olivera, Unraveling the Complexities of Sphingosine-1-Phosphate Function: The Mast Cell Model, 86 Prostaglandins & Other Lipid Mediators 1-11 (2008).
Athanasia Skoura, et al., Sep. 4, 2007, Essential role of sphingosine 1—phosphate receptor 2 in pathological angiogensis of the mouse retina, Research Article, vol. 117, Issue 9, pp. 2506-2516, J Clin Invest.

(Continued)

*Primary Examiner* — Janet L Andres
*Assistant Examiner* — Timothy R Rozof
(74) *Attorney, Agent, or Firm* — Doina G. Ene

(57) ABSTRACT

The invention provides compounds represented by the formula I, each of which compounds may have sphingosine-1-phosphate receptor agonist and or antagonist biological activity, wherein these compounds selected from the group consisting of

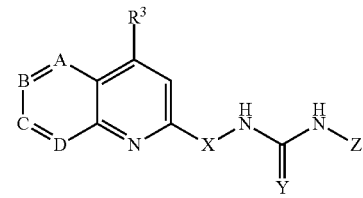

wherein A, B, C, D, X, Y, Z and R$^3$ are defined in the specification. Said compounds are useful for treating a disease or condition of a mammal selected from the group consisting of ocular diseases; systemic vascular barrier related diseases; allergies and other inflammatory diseases; cardiac diseases or conditions; fibrosis; pain and wounds.

12 Claims, No Drawings

(56) References Cited

OTHER PUBLICATIONS

S. Aoki et al., Mar. 26, 2007, The Suppressive Effect of Sphingosine 1-Phosphate on Monocyte-Endothelium Adhesion May be Mediated by the Rearrangement of the Endothelial Integrins. Journal of Thrombosis and Haemostasis, 5, 1292-1301.

Serriere-Lanneau, et al., 2007, The sphingosine 1-phosphate receptor S1P2 triggers hepatic wound healing, Research Communication, 21, 2005-2013, The FASEB Journal.

Suman Mehrotram et al., Sep. 1980, Substituted Thiosemicarbazido/Semicarbazido Quinolines As Possible Antimalarials, Journal of Heterocylcic Chemistry, 17, 1213-1214.

* cited by examiner

CONDENSED RING PYRIDINE COMPOUNDS AS SUBTYPE-SELECTIVE MODULATORS OF SPHINGOSINE-1-PHOSPHATE-2 (S1P$_2$) RECEPTORS

CROSS REFERENCE TO RELATED APPLICATIONS

This application is a divisional application of United States Non-Provisional patent application Ser. No. 13/498,499, filed May 1, 2012, which is a national stage application under 35 U.S.C. §371 of PCT patent application PCT/US10/50486, filed on Sep. 28, 2010, which claims the benefit of U.S. Provisional Patent Application Ser. No. 61/246,642 filed on Sep. 29, 2009, all of which are incorporated herein by reference in their entirety.

BACKGROUND OF THE INVENTION

1. Field of the Invention

The present invention relates to derivatives and/or analogues of sphingosine which are useful as anti-fibrotic drugs and are thereby useful for treating ocular, cardiac, hepatic and pulmonary fibrosis, proliferative vitreoretinopathy, cicatricial pemphigoid, surgically induced fibrosis in cornea, conjunctiva and tenon and for the treatment of eye diseases and conditions.

2. Summary of the Art

Sphingosine is a compound having the chemical structure shown in the general formula described below, in which Y$^1$ is hydrogen. It is known that various sphingolipids, having sphingosine as a constituent, are widely distributed in the living body including on the surface of cell membranes of cells in the nervous system.

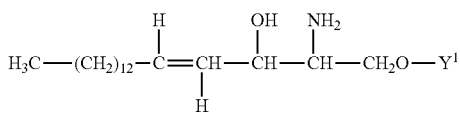

A sphingolipid is one of the lipids having important roles in the living body. A disease called lipidosis is caused by accumulation of a specified sphingolipid in the body. Sphingolipids present on cell membranes function to regulate cell growth; participate in the development and differentiation of cells; function in nerves; are involved in the infection and malignancy of cells; etc. Many of the physiological roles of sphingolipids remain to be solved. Recently the possibility that ceramide, a derivative of sphingosine, has an important role in the mechanism of cell signal transduction has been indicated, and studies about its effect on apoptosis and cell cycle have been reported.

Sphingosine-1-phosphate is an important cellular metabolite, derived from ceramide that is synthesized de novo or as part of the sphingomeyeline cycle (in animals cells). It has also been found in insects, yeasts and plants.

The enzyme, ceramidase, acts upon ceramides to release sphingosine, which is phosphorylated by spingosine kinase, a ubiquitous enzyme in the cytosol and endoplasmic reticulum, to form sphingosine-1-phosphate. The reverse reaction can occur also by the action of sphingosine phosphatases, and the enzymes act in concert to control the cellular concentrations of the metabolite, which concentrations are always low. In plasma, such concentration can reach 0.2 to 0.9 µM, and the metabolite is found in association with the lipoproteins, especially the HDL. It should also be noted that sphingosine-1-phosphate formation is an essential step in the catabolism of sphingoid bases.

Like its precursors, sphingosine-1-phosphate is a potent messenger molecule that perhaps uniquely operates both intra- and inter-cellularly, but with very different functions from ceramides and sphingosine. The balance between these various sphingolipid metabolites may be important for health. For example, within the cell, sphingosine-1-phosphate promotes cellular division (mitosis) as opposed to cell death (apoptosis), which it inhibits. Intracellularly, it also functions to regulate calcium mobilization and cell growth in response to a variety of extracellular stimuli. Current opinion appears to suggest that the balance between sphingosine-1-phosphate and ceramide and/or spingosine levels in cells is critical for their viability. In common with the lysophospholipids, especially lysophosphatidic acid, with which it has some structural similarities, sphingosine-1-phosphate exerts many of its extra-cellular effects through interaction with five specific G protein-coupled receptors on cell surfaces. These are important for the growth of new blood vessels, vascular maturation, cardiac development and immunity, and for directed cell movement.

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular disease. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

Fungi and plants have sphingolipids and the major sphingosine contained in these organisms has the formula described below. It is known that these lipids have important roles in the cell growth of fungi and plants, but details of the roles remain to be solved.

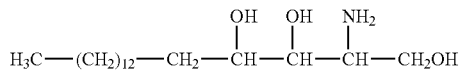

Recently it has been known that derivatives of sphingolipids and their related compounds exhibit a variety of biological activities through inhibition or stimulation of the metabolism pathways. These compounds include inhibitors of protein kinase C, inducers of apoptosis, immuno-suppressive compounds, antifungal compounds, and the like. Substances having these biological activities are expected to be useful compounds for various diseases.

Derivatives of sphingosine have been prepared in various patents. For example, see U.S. Pat. Nos. 4,952,683; 5,110,987; 6,235,912 B1 and 6,239,297 B1.

Also, compounds which are similar to certain spingosine derivatives, but which are not reported as being ligands for the spingosine receptors are reported in various patents and published patent applications. See for example, U.S. Pat. Nos. 5,294,722; 5,102,901; 5,403,851 and 5,580,878. U.S. Patent Application Publication No. U.S. 2003/0125371 A2.

SUMMARY OF THE INVENTION

The present invention provides compounds that are able to regulate the functions of sphingolipid, and pharmaceutical compositions comprising said compounds.

In one aspect of the present invention there are disclosed compounds, having sphingosine-1-phosphate receptor agonist and or antagonist biological activity, represented by the formula I:

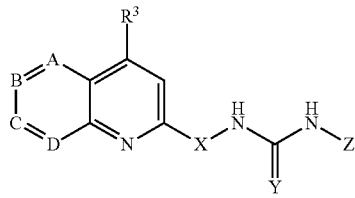

wherein:
wherein A is a direct bond or (CR) and B, C and D are independently selected from the group consisting of (CR) and N, wherein R is H or alkyl, e.g. lower alkyl; provided however, not all, of B, C and D are N and, when A is a direct bond, D is (CR), $R^3$ is selected from the group consisting of alkyl, e.g. lower alkyl;

X is selected from the group consisting of O, $NR^4$ and $CR^4R^5$, wherein $R^4$ and $R^5$ are independently selected from the group consisting of H and alkyl, e.g. lower alkyl;

Y is selected from the group consisting of O or S; and

Z is a substituted aryl ring and pharmaceutically acceptable salts thereof.

In a first aspect of the present invention, the left most ring is a six membered ring, i.e. the compounds of this invention are benzo or pyrido pyridinyl compounds. The compounds included in this first aspect of the invention may be represented by the general formula II, below:

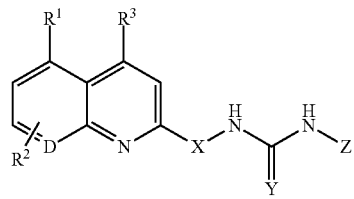

wherein $R^1$ and $R^2$ are independently selected from the group consisting of H and alkyl, e.g. lower alkyl, and may include from 1 to 10 carbons, and may be cyclic or branched chain alkyl radicals having from 3 to 10 carbons; methoxy, hydroxyl, halogen, nitrile, trifluoromethyl and carboxy;

$R^3$ is selected from the group consisting of alkyl, e.g. lower alkyl, and may include from 1 to 10 carbons, and may be cyclic or branched chain alkyl radicals having from 3 to 10 carbons; methoxy, hydroxyl, halogen, nitrile, trifluoromethyl and carboxy;

D is CR or N;

X is O, $NR^4$ or $CR^4R^5$, where $R^4$, $R^5$ are independently selected from the group consisting of H and alkyl, e.g. lower alkyl and may have from 1 to 10 carbons, and may be cyclic or branched chain alkyl having 3 to 10 carbons, methoxy, hydroxyl, F, Br, I, nitrile, trifluoromethyl and carboxy;

Y is O or S, preferably O;

Z is a substituted aryl ring, e.g. a carbocyclic or heterocyclic aryl ring, having the following structure:

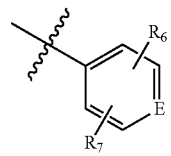

wherein $R^6$ and $R^7$ are independently selected from the group consisting of alkyl and may include from 1 to 10 carbons, and may be cyclic or branched chain alkyl having 3 to 10 carbons, alkyloxy, preferably lower alkyloxy, e.g. ethyloxy, isopropyloxy, n-butyloxy; hydroxyl, halogen, preferably chloro; nitrile, trifluoromethyl, and carboxy; and E is N or CR, preferably N In a second aspect, of the present invention, the compounds of this invention the left most ring is a five membered ring, i.e. the compounds are 1-H pyrazolo[4,3-b]pyridinyl compounds. The compounds included in this second aspect of the invention may be represented by the general formula III:

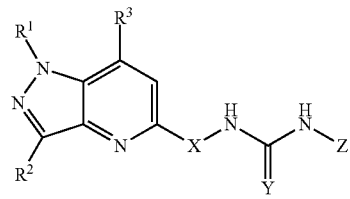

wherein $R^1$, $R^2$ and $R^3$ are independently selected from the group consisting of H and alkyl, e.g. lower alkyl, and may include from 1 to 10 carbons, and may be cyclic or branched chain alkyl radicals having from 3 to 10 carbons; methoxy, hydroxyl, halogen, nitrile, trifluoromethyl and carboxy;

$R^3$ is selected from the group consisting of alkyl, e.g. lower alkyl, and may include from 1 to 10 carbons, and may be cyclic or branched chain alkyl radicals having from 3 to 10 carbons; methoxy, hydroxyl, halogen, nitrile, trifluoromethyl and carboxy;

D is CR or N;

X is O, $NR^4$, or $CR^4R^5$, where $R^4$, $R^5$ are independently selected from the group consisting of H and alkyl, e.g. lower alkyl and may have from 1 to 10 carbons, and may be cyclic or branched chain alkyl having 3 to 10 carbons, methoxy, hydroxyl, F, Br, I, nitrile, trifluoromethyl and carboxy;

Y is O or S, preferably O;

Z is a substituted aryl ring, e.g. a carbocyclic or heterocyclic aryl ring, having the following structure:

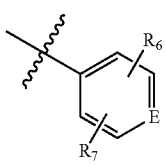

wherein $R^6$ and $R^7$ are independently selected from the group consisting of alkyl and may include from 1 to 10 carbons, and may be cyclic or branched chain alkyl having 3 to 10 carbons, alkyloxy, preferably lower alkyloxy, e.g. ethyloxy, isopropyloxy, n-butyloxy; hydroxyl, halogen, preferably chloro; nitrile, trifluoromethyl, and carboxy; and E is N or CR, preferably N;

Preferably, Z is a disubstituted aryl, more preferably an o,o-substituted pyridinyl.

In another aspect of this invention, there is disclosed a method of treating or preventing a disease or condition selected from the group consisting of fibrotic conditions e.g.; ocular, cardiac, hepatic and pulmonary fibrosis, proliferative vitreoretinopathy, cicatricial pemphigoid, surgically induced fibrosis in cornea, conjunctiva and tenon which comprises administering to a patient in need thereof a compound represented by the formula I, II, or III, above.

DETAILED DESCRIPTION OF THE INVENTION

Novel compounds having this general structure were synthesized and tested for sphingosine 2-phosphate receptor activity using the FLIPR assay. Cells expressing the receptor of interest ($S1P_1$, $S1P_2$ or $S1P_3$) and a G-protein (Gqi5 or G16) are loaded with fluo-4, a calcium sensitive dye. After removal of excess dye by washing, the cells are placed in the FLIPR TETRA instrument. Baseline fluorescence readings are taken prior to addition the compound to be tested. Agonists will trigger the receptor to interact with the G-protein, leading to an increase in intracellular calcium. The increase in intracellular calcium causes an increase in the fluorescence of the cells, due to the presence of fluo-4. This fluorescence increase is recorded by the FLIPR TETRA. After the calcium transient signal has decreased towards baseline, the standard agonist sphingosine 1-phosphate is added. If the test compound is an antagonist, an initial calcium signal will not be generated and the antagonist will prevent the generation of a calcium signal from sphingosine 1-phosphate. The level of fluorescence is compared to that of sphingosine 1-phosphate, and the EC50 or IC50 of the compound determined by curve fitting.

The compounds in this invention are useful for the treatment of mammals, including humans, for diseases or conditions selected from the group consisting of ocular, cardiac, hepatic and pulmonary fibrosis, proliferative vitreoretinopathy, cicatricial pemphigoid, surgically induced fibrosis in cornea, conjunctiva and tenon Specific Examples of the compounds of formula I include the compounds of Table 1, below.

TABLE 1

| Example Number | Structure |
|---|---|
| 1 | (structure: 1,3-dimethyl-7-isopropyl-pyrazolo[4,3-b]pyridine linked via N-NH-C(=O)-NH to 3,5-dichlorophenyl) |
| 2 | (structure: 1,3-dimethyl-7-isopropyl-pyrazolo[4,3-b]pyridine linked via CH2-NH-C(=O)-NH to 2,6-dichloropyridin-4-yl) |
| 3 | (structure: 1,3-dimethyl-7-isopropyl-pyrazolo[4,3-b]pyridine linked via N-NH-C(=O)-NH to 2-butyl-6-chloropyridin-4-yl) |

TABLE 1-continued
| Example Number | Structure |
|---|---|
| 4 | 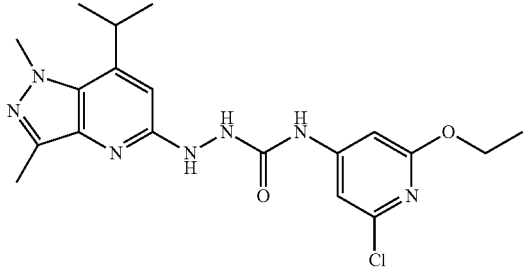 [SMILES: CCOc1cc(NC(=O)NNc2cc(C(C)C)c3c(n2)c(C)nn3C)cc(Cl)n1] |
| 5 | 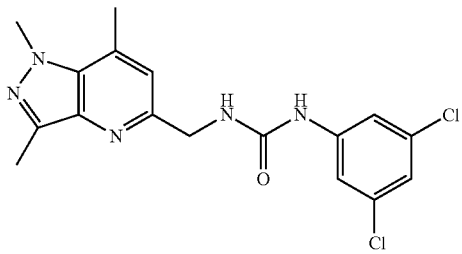 |
| 6 | 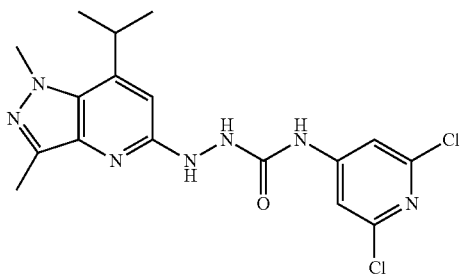 [SMILES: Cc1nn(C)c2c(C(C)C)cc(NNC(=O)Nc3cc(Cl)nc(Cl)c3)nc12] |
| 7 | 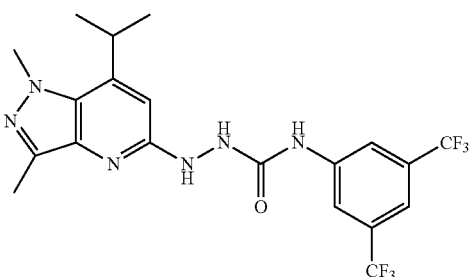 |
| 8 | 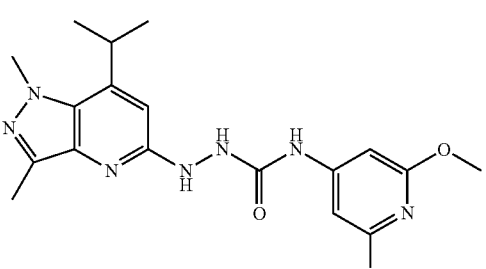 |

TABLE 1-continued
| Example Number | Structure |
|---|---|
| 9 | 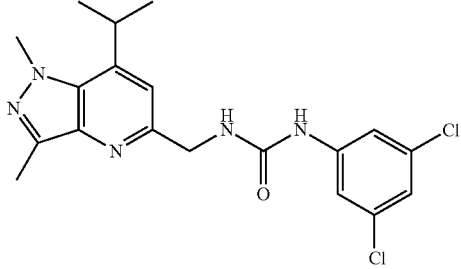 [SMILES: Cc1nn(C)c2c(C(C)C)cc(CNC(=O)Nc3cc(Cl)cc(Cl)c3)nc12] |
| 10 | 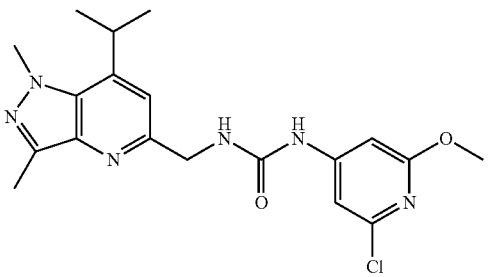 [SMILES: COc1cc(NC(=O)NCc2cc(C(C)C)c3c(n2)c(C)nn3C)cc(Cl)n1] |
| 11 | 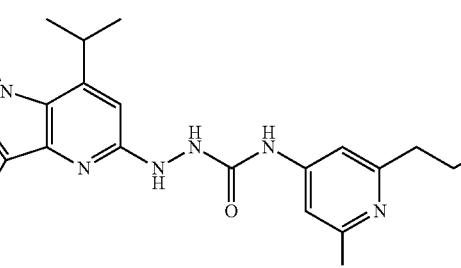 |
| 12 | 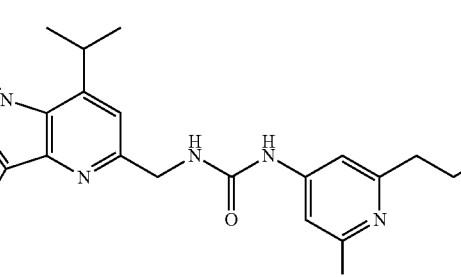 |
| 13 | 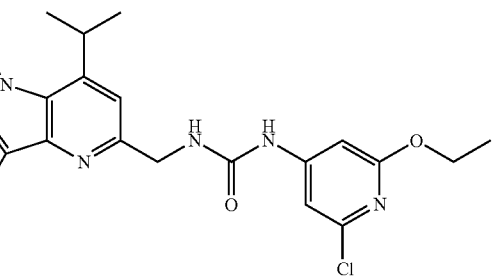 |

TABLE 1-continued
| Example Number | Structure |
|---|---|
| 14 | 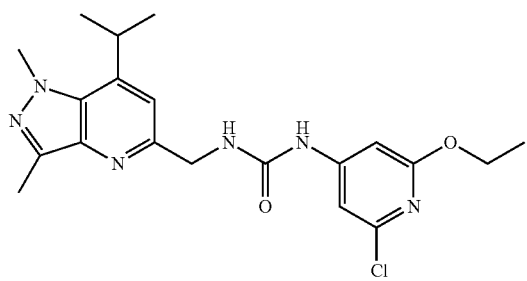 [SMILES: CCOc1cc(NC(=O)NCc2cc(C(C)C)c3c(n2)c(C)nn3C)cc(Cl)n1] |
| 15 | 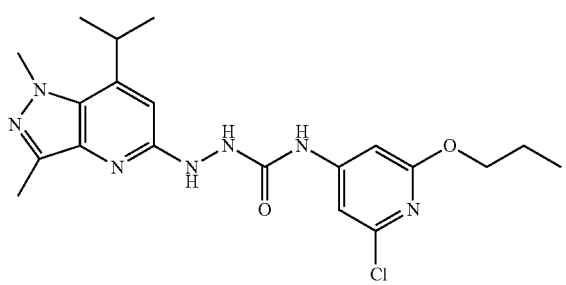 [SMILES: CCCOc1cc(NC(=O)NNc2cc(C(C)C)c3c(n2)c(C)nn3C)cc(Cl)n1] |
| 16 | 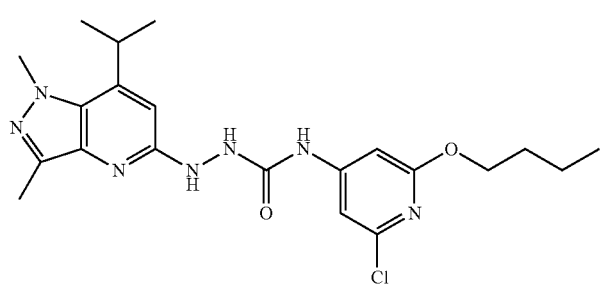 [SMILES: CCCCOc1cc(NC(=O)NNc2cc(C(C)C)c3c(n2)c(C)nn3C)cc(Cl)n1] |
| 17 | 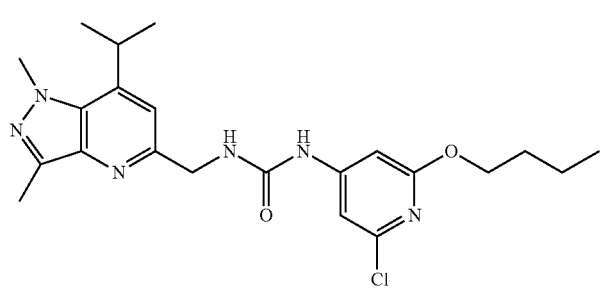 [SMILES: CCCCOc1cc(NC(=O)NCc2cc(C(C)C)c3c(n2)c(C)nn3C)cc(Cl)n1] |
| 18 | 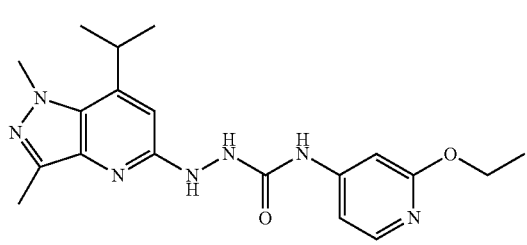 [SMILES: CCOc1cc(NC(=O)NNc2cc(C(C)C)c3c(n2)c(C)nn3C)ccn1] |

TABLE 1-continued
| Example Number | Structure |
|---|---|
| 19 | 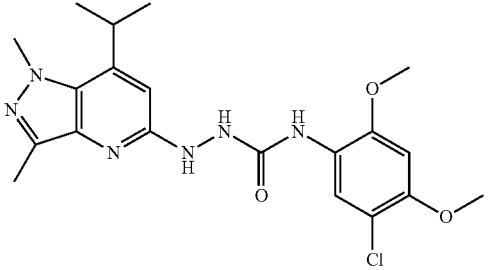 [SMILES: COc1cc(OC)c(NC(=O)NNc2cc(C(C)C)c3c(n2)c(C)nn3C)cc1Cl] |
| 20 | 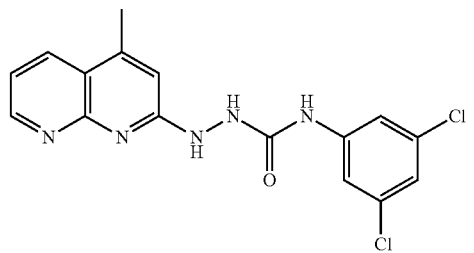 [SMILES: Cc1cc(NNC(=O)Nc2cc(Cl)cc(Cl)c2)nc2ncccc12] |
| 21 | 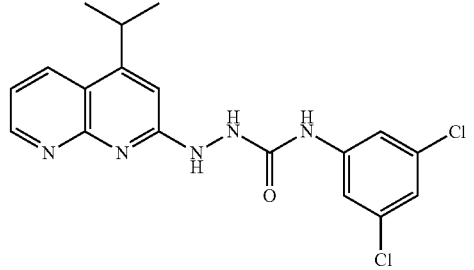 [SMILES: CC(C)c1cc(NNC(=O)Nc2cc(Cl)cc(Cl)c2)nc2ncccc12] |
| 22 | 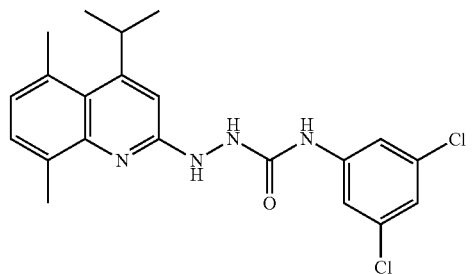 [SMILES: Cc1ccc(C)c2c(C(C)C)cc(NNC(=O)Nc3cc(Cl)cc(Cl)c3)nc12] |
| 23 | 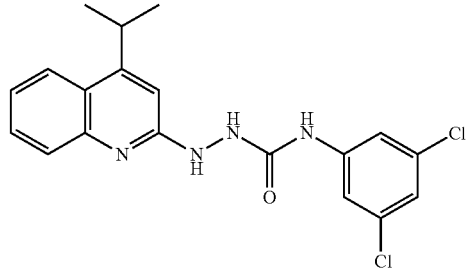 [SMILES: CC(C)c1cc(NNC(=O)Nc2cc(Cl)cc(Cl)c2)nc2ccccc12] |

TABLE 1-continued

| Example Number | Structure |
| --- | --- |
| 24 | (4,8-dimethylquinolin-2-yl)-semicarbazide linked to N-(2,6-dichloropyridin-4-yl)urea |
| 25 | (4,8-dimethylquinolin-2-yl)-semicarbazide linked to N-(3,5-dichlorophenyl)urea |
| 26 | (4-methylquinolin-2-yl)-semicarbazide linked to N-(2,6-dichloropyridin-4-yl)urea |
| 27 | (4,5,8-trimethylquinolin-2-yl)-semicarbazide linked to N-(3,5-dichlorophenyl)urea |

Some compounds within the scope of the invention may be prepared as depicted in the procedures described below.

The invention is further illustrated by the following examples which are illustrative of a specific mode of practicing the invention and are not intended as limiting the scope of the claims.

Unless otherwise indicated, the following terms as used throughout this specification have the following meanings:

DCM refers to dichloromethane
THF refers to tetrahydrofuran
EtOAc refers to ethylacetate
"Me" refers to methyl.
"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents selected from the group consisting of hydroxyl, cyano, alkoxy, =O, =S, $NO_2$, halogen, dimethyl amino and SH.

"Alkoxy" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic" refers to cyclic saturated or unsaturated aliphatic hydrocarbon and aryl hydrocarbon groups wherein the ring atoms are exclusively carbons, and comprises from 6 to 20 carbon atoms, including said ring atoms.

"Carbocyclic aryl" refers to an aryl group wherein the ring atoms are carbon.

"Heterocyclic" refers to cyclic groups wherein the ring atoms comprise carbon atoms and at least one oxygen, nitrogen, and/or sulfur atom and may be saturated, unsaturated, i.e. have one or more double bonds, or aryl, and comprises up to 20 carbon atoms and from 1 to 5 of the above heteroatoms.

"Heterocyclic aryl" refers to an aryl group having from 1 to 3 heteroatoms as ring atoms, the remainder of the ring atoms being carbon. Heteroatoms include oxygen, sulfur, and nitrogen.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, amide, ester, thioamide, thiol ester, amine, thioether, sulfonyl, etc.

"Amide" refers to —C(O)—NH—R', wherein R' is alkyl, aryl, alkylaryl or hydrogen.

"Ester" refers to —C(O)—O—R', wherein R' is alkyl, aryl or alkylaryl.

"Thioamide" refers to —C(S)—NH—R', wherein R' is alkyl, aryl, alkylaryl or hydrogen.

"Thiol ester" refers to —C(O)—S—R', wherein R' is alkyl, aryl, alkylaryl or hydrogen.

"Amine" refers to a—N(R")R''' group, wherein R" and R' are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R", where R"" is aryl, C(CN)═C-aryl, CH$_2$CN, alkyaryl, sulfonamide, NH-alkyl, NH-alkylaryl, or NH-aryl.

Also, alternatively the substituent on the phenyl moiety may be referred to as an o, m or p substituent or a 2, 3 or 4 substituent, respectively. (Obviously, the 5 substituent is also a meta substituent and the 6 substituent is an ortho substituent.)

The above compounds are evaluated for S1P2 activity according to the above assay: The results are reported in TABLE 2, below.

Proton nuclear magnetic resonance ($^1$H NMR) and carbon nuclear magnetic resonance ($^{13}$C NMR) spectra were recorded on a Varian 300 or 500 MHz spectrometer in deuterated solvent. Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; m, multiplet; br, broad. Data were reported in the following format: chemical shift (multiplicity, coupling constant(s) J in hertz (Hz), integrated intensity).

General Procedure A for the Synthesis of Substituted 4-Isocyanatopyridine Intermediates

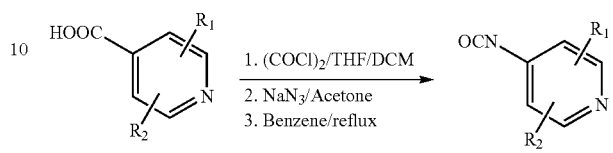

Commercially available properly substituted isonicotinic acid (1.87 mmol) was dissolved in THF:DCM (4:10 ml) at 0° C. Oxalyl chloride (2.0M in DCM, 1.87 ml, 3.75 mmol) was added followed by 2 drops of DMF. The resulting solution was stirred at 0° C. for 30 min and concentrated to dryness. The solid was dissolved in 10 ml of acetone and cooled to 0° C. NaN$_3$ (195 mg, 3.00 mmol) in 1 mL of water was added. After stirring at 0° C. for 30 min, the reaction mixture was concentrated again to dryness and re-dissolved in benzene which was washed quickly with ice cold water and dried over Na$_2$SO$_4$. The drying agent Na$_2$SO$_4$ was filtered out, and the filtrate was stirred at 110° C. then cooled to 50° C. to generate the title compound in situ. This crude isocyanate was used in the subsequent transformation without further purification.

Syntheses of 5-hydrazinyl-7-isopropyl-1,3-dimethyl-1H-pyrazolo[4,3-b]pyridine and (7-isopropyl-1,3-dimethyl-1H-pyrazolo[4,3-b]pyridin-5-yl)methanamine intermediates The title intermediate compounds were prepared from commercially available 3-fluoropyridine according to the following scheme.

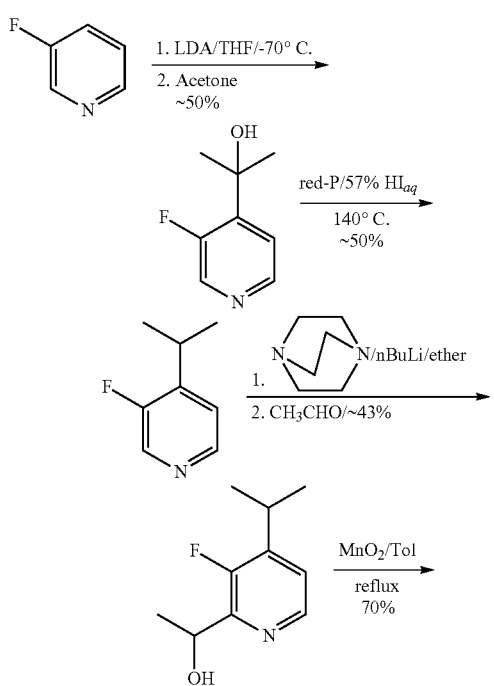

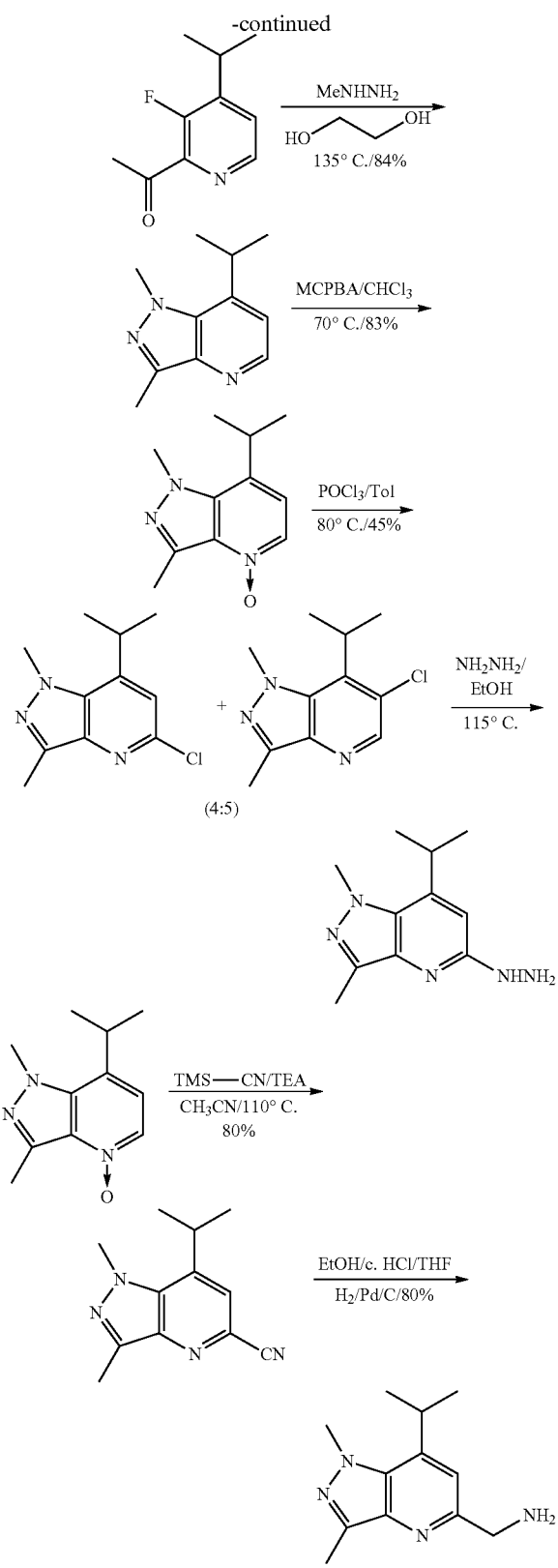

reaction was then quenched with aqueous NH₄Cl and extracted with ether. The combined organic layers were washed with H₂O and brine, then dried over Na₂SO₄ and concentrated under vacuum. Purification by MPLC (80 g column, 0 to 40% ethyl acetate in hexane as eluant) afforded the title compound. Spectroscopic data: $^1$H-NMR (300 MHz, CDCl₃): δ ppm 1.65 (s, 6 H), 7.27 (dd, J=5.57 Hz, 1 H), 8.36-8.39 (m, 2 H).

3-Fluoro-4-isopropyl-pyridine: 2-(3-Fluoro-pyridin-4-yl)-propan-2-ol (from the previous step, 6.40 g, 41.3 mmol) was dissolved in 50 mL of 57% HI aqueous solution. Red phosphorus (4.48 g, 144.0 mmol) was added and the mixture was stirred at 140° C. for 5 hours. The reaction mixture was cooled to room temperature, neutralized with 5N aq NaOH and extracted with ether. The combined organic layers were washed with H₂O and brine, then dried over Na₂SO₄ and concentrated under vacuum. The title compound was obtained by distillation. Spectroscopic data: $^1$H-NMR (300 MHz, CDCl₃): δ ppm 1.27 (d, J=7.04 Hz, 6 H), 3.25 (hept, J=7.04 Hz, 1 H), 7.21 (dd, J=5.44 Hz, 1 H), 8.33-8.36 (m, 2 H).

1-(3-Fluoro-4-isopropyl-pyridin-2-yl)-ethanol: 1,4-diazabicyclo[2,2,2]octane (6.16 g, 55.0 mmol) was dissolved in ether (100 mL) at −40° C. n-BuLi (2.5M in hexane, 57.50 mL, 23.0 mmol) was added and the resulting reaction mixture was stirred at −20° C. for 1 hour. The reaction solution was then cooled to −60° C. and 3-fluoro-4-isopropyl-pyridine (obtained from the previous step, 7.00 g, 50.0 mmol) was introduced. The stirring was continued for 1 hour and acetaldehyde (3 mL) was added. The solution was then allowed to warm up to −30° C. in 1 hour and quenched with aqueous NH₄Cl. The aqueous layer was extracted with ether. The combined extract was dried over Na₂SO₄ and concentrated. Purification by MPLC (80 g column, 0 to 15% ethyl acetate in hexane as eluant) afforded the title compound. Spectroscopic data: $^1$H-NMR (300 MHz, CDCl₃): δ ppm 1.27 (d, J=7.04 Hz, 3 H), 1.29 (d, J=7.04 Hz, 3 H), 1.50 (d, J=6.44 Hz, 3 H), 3.28 (hept, J=7.04 Hz, 1 H), 5.13 (q, J=6.44 Hz, 3 H), 7.18 (dd, J=5.41 Hz, 1 H), 8.29 (d, J=5.27 Hz, 1 H).

1-(3-Fluoro-4-isopropyl-pyridin-2-yl)-ethanone: 1-(3-Fluoro-4-isopropyl-pyridin-2-yl)-ethanol (prepared in the previous step, 3.00 g, 16.39 mmol) was dissolved in 60 mL of anhydrous toluene. MnO₂ (4.05 g, 46.55 mmol) was added and the resulting mixture was stirred at 140° C. overnight. The mixture was then cooled to room temperature and filtered thought a pad of celite. The filtrate was concentrated and purified via MPLC (80 g, 0 to 20% ethyl acetate in hexane) to afford the title compound. Spectroscopic data: $^1$H-NMR (300 MHz, CDCl₃): δ ppm 1.28 (d, J=6.73 Hz, 6 H), 2.70 (s, 3 H), 3.35 (hept, J=6.73 Hz, 1 H), 7.38 (dd, J=5.13 Hz, 1 H), 8.39 (d, J=4.69 Hz, 1 H).

7-Isopropyl-1,3-dimethyl-1H-pyrazolo[4,3-b]pyridine: 1-(3-Fluoro-4-isopropyl-pyridin-2-yl)-ethanone (prepared in the previous step, 2.50 g, 15.15 mmol) and methyl hydrazine (1.04 g, 23.00 mmol) were combined in 8 mL of glycol. The reaction solution was stirred at 140° C. for 2 hours. After cooling, it was quenched with water, extracted with DCM, then washed with water, brine and concentrated. Column chromatography using 15 to 35% ethyl acetate in hexane as eluant afforded the title compound as a pale yellow solid. Spectroscopic data: $^1$H-NMR (300 MHz, CDCl₃): δ ppm 1.39 (d, J=6.73 Hz, 6 H), 2.64 (s, 3 H), 3.65 (hept, J=6.73 Hz, 1 H), 4.23 (s, 3 H), 7.14 (d, J=4.69 Hz, 1 H), 8.44 (d, J=4.69 Hz 1 H).

7-Isopropyl-1,3-dimethyl-1H-pyrazolo[4,3-b]pyridine 4-oxide: To 7-isopropyl-1,3-dimethyl-1H-pyrazolo[4,3-b]pyridine (prepared in the previous step, 2.50 g, 13.22 mmol)

2-(3-Fluoro-pyridin-4-yl)-propan-2-ol: 3-Fluoropyridine (11.0 g, 113.0 mmol) in 100 mL of THF was treated with LDA (1.5M, 100.0 mL, 150.0 mmol) at −78° C. for 50 min under argon. Acetone (28 mL) was added and the resulting reaction mixture was stirred at −78° C. to −40° C. for 50 min. The in 100 mL of chloroform was added 77% MCPBA (5.91 g, 26.44 mmol) at 0° C. The resulting solution was stirred at 90° C. for 3 hours. After cooling, it was neutralized with aq NaHCO$_3$ and extracted with DCM thoroughly. The combined organic phases were then washed with water, brine and concentrated. Column chromatography using 5% 7N NH$_3$ in MeOH/DCM as eluant afforded the title compound as a white solid. Spectroscopic data: $^1$H-NMR (300 MHz, CDCl$_3$): δ ppm 1.37 (d, J=6.73 Hz, 6 H), 2.83 (s, 3 H), 3.60 (hept, J=6.73 Hz, 1 H), 4.21 (s, 3 H), 6.78 (d, J=6.30 Hz, 1 H), 8.01 (d, J=6.30 Hz 1 H).

5-Chloro-7-isopropyl-1,3-dimethyl-1H-pyrazolo[4,3-b]pyridine: To a solution of 7-isopropyl-1,3-dimethyl-1H-pyrazolo[4,3-b]pyridine 4-oxide (obtained from the previous step, 2.26 g, 11.00 mmol) in 30 mL of toluene was added POCl$_3$ (3.37 g, 22.00 mmol). The resulting reaction mixture was stirred at 90° C. for 2 hours and then concentrated. DCM was added. The organic layer was washed with water and brine, then dried over Na$_2$SO$_4$ and concentrated. Column chromatography with DCM separated two isomers and afforded the title compound as a white solid. Spectroscopic data: $^1$H-NMR (300 MHz, CDCl$_3$): δ ppm 1.39 (d, J=6.73 Hz, 6 H), 2.58 (s, 3 H), 3.62 (hept, J=6.73 Hz, 1 H), 4.21 (s, 3 H), 7.11 (s, 1 H).

(7-Isopropyl-1,3-dimethyl-1H-pyrazolo[4,3-b]pyridin-5-yl)-hydrazine: 5-Chloro-7-isopropyl-1,3-dimethyl-1H-pyrazolo[4,3-b]pyridine (obtained from the previous step, 620 mg, 2.68 mmol) and 6 mL of hydrazine monohydrate were combined in 4 mL of EtOH. The reaction solution was stirred at 120° C. for 3 days. The reaction solution was then concentrated under reduced pressure. MeOH was added to the residue and concentrated again. Repetition of this procure several times until some solid formed. The solid was collected by filtration as the title compound. Spectroscopic data: $^1$H-NMR (300 MHz, CDCl$_3$): δ ppm 1.34 (d, J=6.73 Hz, 6 H), 2.52 (s, 3 H), 3.56 (hept, J=6.73 Hz, 1H), 4.15 (s, 3 H), 6.59 (s, 1 H).

7-Isopropyl-1,3-dimethyl-1H-pyrazolo[4,3-b]pyridine-5-carbonitrile: To a solution of 7-isopropyl-1,3-dimethyl-1H-pyrazolo[4,3-b]pyridine N-oxide (obtained from the previous step, 1.06 g, 5.17 mmol) and TEA (1.08 mL, 7.73 mmol) in 20 mL CH$_3$CN was added TMS cyanide (1.37 g, 10.34 mmol). The resulting solution was stirred at reflux for 18 hours. Another 0.5 mL of TMS cyanide was added and the reaction continued for another 7 hours. The solvent was removed under reduced pressure and the residue was loaded to silica gel column and eluted with 20 to 30% ethyl acetate to afford the desired title compound as a solid. Spectroscopic data: $^1$H-NMR (300 MHz, CDCl$_3$): δ ppm 1.40 (d, J=6.74 Hz, 6 H), 2.64 (s, 3 H), 3.69 (hept, J=6.74 Hz, 1 H), 4.26 (s, 3 H), 7.46 (s, 1 H).

C-(7-Isopropyl-1,3-dimethyl-1H-pyrazolo[4,3-b]pyridin-5-yl)-methylamine: 7-Isopropyl-1,3-dimethyl-1H-pyrazolo[4,3-b]pyridine-5-carbonitrile (from the previous step, 91.05 g, 5.15 mmol) was dissolved in EtOH:THF:conc.HCl (25 mL:10 mL:1.5 mL). 400 mg of 10% Pd/C was added and the reaction mixture was stirred under hydrogen balloon overnight. The catalyst was filtered out and the filtrate was concentrated under reduced pressure to afford the title compound as a white solid. Spectroscopic data: $^1$H-NMR (300 MHz, CD$_3$OD): δ ppm 1.41 (d, J=6.74 Hz, 6 H), 2.56 (s, 3 H), 3.77 (hept, J=6.74 Hz, 1 H), 4.02 (s, 2 H), 4.21 (s, 3 H), 7.36 (s, 1 H).

General Procedure B for the Synthesis of Substituted Ureas

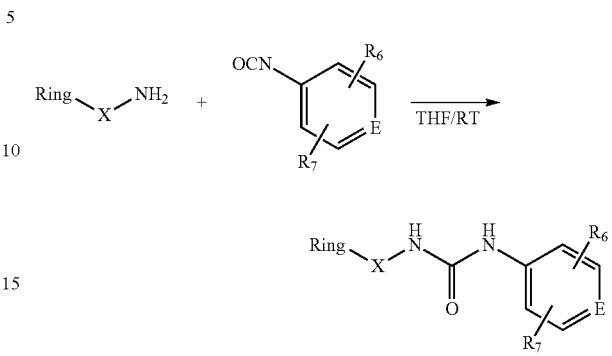

A properly substituted amine or hydrazine prepared above and a properly substituted isocyanate (either commercial or prepared above, 1.1 eq) were dissolved in 8 mL of THF. The reaction mixture was stirred at room temperature for 4 hours and the solvent was removed under reduced pressure. The title compound was isolated by column chromatography using 30 to 75% ethyl acetate in hexane, further purified by recrystallization from MeOH.

Example 1

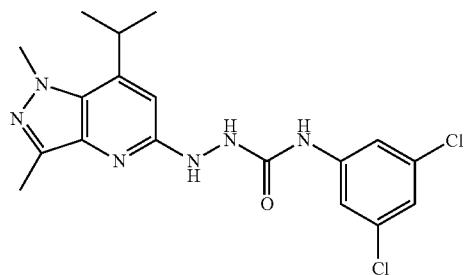 [SMILES: Cc1nn(C)c2c(C(C)C)cc(NNC(=O)Nc3cc(Cl)cc(Cl)c3)nc12]

Synthesis of N-(3,5-dichlorophenyl)-2-(7-isopropyl-1,3-dimethyl-1H-pyrazolo[4,3-b]pyridin-5-yl)hydrazinecarboxamide The title compound was generated from (7-isopropyl-1,3-dimethyl-1H-pyrazolo[4,3-b]pyridin-5-yl)-hydrazine prepared above and commercially available 3,5-dichlorophenyl isocyanate according to General procedure B described above.

N-(3,5-Dichlorophenyl)-2-(7-isopropyl-1,3-dimethyl-1H-pyrazolo[4,3-b]pyridin-5-yl)hydrazinecarboxamide: The title compound was obtained from 3,5-dichlorophenyl isocyanate (commercially available, 113 mg, 0.60 mmol), 5-hydrazinyl-7-isopropyl-1,3-dimethyl-1H-pyrazolo[4,3-b]pyridine (prepared above, 110 mg, 0.50 mmol) according to the protocols as outlined in general procedure B above. Spectroscopic Data: $^1$H NMR (300 MHz, CD$_3$OD) δ ppm 1.38 (d, J=6.73 Hz, 6 H), 2.44 (s, 3 H), 3.70 (hept, J=6.73 Hz, 1 H), 4.14 (s, 3 H), 6.85 (s, 1 H), 7.02 (dd, J=1.76 Hz, 1 H), 7.55 (d, J=1.76 Hz, 2 H).

Example 2

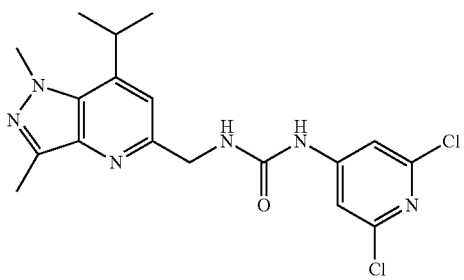

Synthesis of 1-(2,6-dichloropyridin-4-yl)-3-((7-isopropyl-1,3-dimethyl-1H-pyrazolo[4,3-b]pyridin-5-yl)methyl)urea The title compound was generated from (7-isopropyl-1,3-dimethyl-1H-pyrazolo[4,3-b]pyridin-5-yl)methanamine prepared above and commercially available 2,6-dichloro-4-isocyanatopyridine according to General procedure B described above.

1-(2,6-Dichloropyridin-4-yl)-3-((7-isopropyl-1,3-dimethyl-1H-pyrazolo[4,3-h]pyridin-5-yl)methyl)urea: The title compound was obtained from 2,6-dichloro-4-isocyanatopyridine (commercially available, 180 mg, 0.95 mmol), (7-isopropyl-1,3-dimethyl-1H-pyrazolo[4,3-b]pyridin-5-yl) methanamine (prepared above, 200 mg, 0.92 mmol) according to the protocols as outlined in general procedure B above. Spectroscopic Data: $^1$H NMR (300 MHz, CD$_3$OD) δ ppm 1.40 (d, J=6.73 Hz, 6 H), 2.57 (s, 3 H), 3.74 (hept, J=6.73 Hz, 1 H), 4.22 (s, 3 H), 4.61 (s, 2 H), 7.33 (s, 1 H), 7.48 (s, 2 H).

Example 3

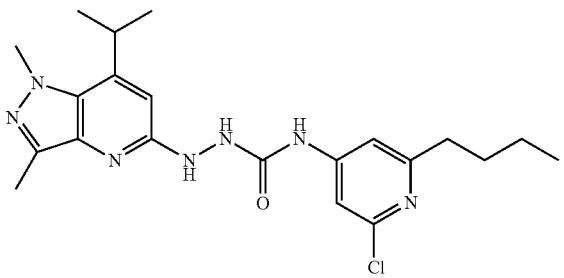 [SMILES: CCCCc1cc(NC(=O)NNc2cc(C(C)C)c3c(n2)c(C)nn3C)cc(Cl)n1]

Synthesis of N-(2-butyl-6-chloropyridin-4-yl)-2-(7-isopropyl-1,3-dimethyl-1H-pyrazolo[4,3-b]pyridin-5-yl)hydrazinecarboxamide The title compound was generated from (7-isopropyl-1,3-dimethyl-1H-pyrazolo[4,3-b]pyridin-5-yl)-hydrazine prepared above and 2-butyl-6-chloro-4-isocyanato-pyridine according to General procedure B described above. Intermediate 2-butyl-6-chloro-4-isocyanato-pyridine was prepared according to general procedure A and used in situ without further purification.

2-Butyl-6-chloro-isonicotinic acid: The titled compound was prepared from ethyl 2,4-dioxooctanate according to the literature reported method in reference 1. The spectroscopic data match those reported in the reference and also reported here: $^1$H-NMR (300 MHz, CD$_3$OD): δ ppm 0.96 (t, J=7.33 Hz, 3 H), 1.33-1.43 (m, 2 H), 1.66-1.76 (m, 2 H), 2.82 (t, J=7.62 Hz, 2 H), 7.70 (s, 1 H).

2-Butyl-6-chloro-4-isocyanato-pyridine: The title compound was prepared from butyl-6-chloro-isonicotinic acid (prepared above, 400 mg, 1.87 mmol), oxalyl chloride (2.0 M in DCM, 1.87 mL, 3.75 mmol) according to general procedure A described above. The crude title compound was used in the next step without further purification.

N-(2-Butyl-6-chloropyridin-4-yl)-2-(7-isopropyl-1,3-dimethyl-1H-pyrazolo[4,3-h]pyridin-5-yl)hydrazinecarboxamide: The title compound was obtained from 2-butyl-6-chloro-4-isocyanato-pyridine (prepared above), 5-hydrazinyl-7-isopropyl-1,3-dimethyl-1H-pyrazolo[4,3-b]pyridine (prepared above, 200 mg, 0.92 mmol) according to the protocols as outlined in general procedure B above. Spectroscopic Data: $^1$H NMR (300 MHz, CD$_3$OD) δ ppm 0.91 (t, J=7.32 Hz, 3 H), 126 (m, 2 H), 1.35 (d, J=6.73 Hz, 6 H), 1.61 (m, 2 H), 2.43 (s, 3 H), 2.61 (t, J=7.68 Hz, 2 H), 3.65 (hept, J=6.73 Hz, 1 H), 4.12 (s, 3 H), 6.82 (s, 1 H), 7.30 (s, 1 H), 7.55 (s, 1 H).

Example 4

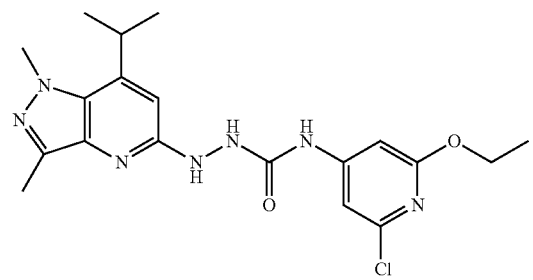 [SMILES: CCOc1cc(NC(=O)NNc2cc(C(C)C)c3c(n2)c(C)nn3C)cc(Cl)n1]

Synthesis of N-(2-chloro-6-ethoxypyridin-4-yl)-2-(7-isopropyl-1,3-dimethyl-1H-pyrazolo[4,3-b]pyridin-5-yl)hydrazinecarboxamide The title compound was generated from (7-isopropyl-1,3-dimethyl-1H-pyrazolo[4,3-b]pyridin-5-yl)-hydrazine prepared above and 2-chloro-6-ethoxy-4-isocyanatopyridine according to General procedure B described above. Intermediate 2-chloro-6-ethoxy-4-isocyanatopyridine was prepared according to general procedure A and used in situ without further purification.

2-Chloro-6-ethoxy-isonicotinic acid: The titled compound was prepared from 2.6-dichloropyridine-4-carboxylic acid according to the reported method in reference 2. The spectroscopic data match those reported in the reference and also listed here $^1$H-NMR (300 MHz, CD$_3$OD): ppm 1.38 (t, J=7.04 Hz, 3 H), 4.36 (q, J=7.04 Hz, 2 H), 7.17 (d, J=1.18 Hz, 1 H), 7.39 (d, J=1.18 Hz, 1 H).

2-Chloro-6-ethoxy-4-isocyanato-pyridine: The title compound was prepared from 2-chloro-6-ethoxy-isonicotinic acid (prepared above), oxalyl chloride (2.0 M in DCM)

according to general procedure A described above. The crude title compound was used in the next step without further purification.

N-(2-Chloro-6-ethoxypyridin-4-yl)-2-(7-isopropyl-1,3-dimethyl-1H-pyridin[4,3-h]pyridin-5-yl)hydrazinecarboxamide: The title compound was obtained from 2-chloro-6-ethoxy-4-isocyanato-pyridine (prepared above), 5-hydrazinyl-7-isopropyl-1,3-dimethyl-1H-pyrazolo[4,3-b]pyridine (prepared above, 180 mg, 0.82 mmol) according to the protocols as outlined in general procedure B above. Spectroscopic Data: $^1$H NMR (300 MHz, CD$_3$OD) δ ppm 1.33 (t, J=7.04 Hz, 3 H), 1.37 (d, J=6.73 Hz, 6 H), 2.44 (s, 3 H), 3.67 (hept, J=6.73 Hz, 1 H), 4.14 (s, 3 H), 4.24 (q, J=7.04 Hz, 2 H), 6.83 (s, 1 H), 6.92 (s, 1 H), 7.10 (s, 1 H).

Example 5

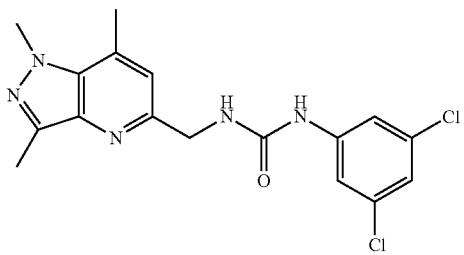 [SMILES: Cc1nn(C)c2c(C)cc(CNC(=O)Nc3cc(Cl)cc(Cl)c3)nc12]

Synthesis of 1-(3,5-dichlorophenyl)-3-((1,3,7-trimethyl-1H-pyrazolo[4,3-b]pyridin-5-yl)methyl)urea The title compound was generated from (1,3,7-trimethyl-1H-pyrazolo[4,3-b]pyridin-5-yl)methanamine prepared using the procedure described above for (7-isopropyl-1,3-dimethyl-1H-pyrazolo[4,3-b]pyridin-5-yl)methanamine and commercially available 3,5-dichlorophenyl isocyanate according to General procedure B described above.

1-(3,5-Dichlorophenyl)-3-((1,3,7-trimethyl-1H-pyrazolo[4,3-b]pyridin-5-yl)methyl)urea: The title compound was obtained from 3,5-dichlorophenyl isocyanate (commercially available, 170 mg, 0.90 mmol), (1,3,7-trimethyl-1H-pyrazolo[4,3-b]pyridin-5-yl)methanamine (prepared above, 160 mg, 0.84 mmol) according to the protocols as outlined in general procedure B above. Spectroscopic Data: $^1$H NMR (300 MHz, CD$_3$OD) δ ppm 2.47 (s, 3 H), 2.74 (s, 3 H), 4.14 (s, 3 H), 4.47 (d, J=4.69 Hz, 2 H), 7.01 (dd, J=2.07 Hz, 1 H), 7.10 (bs, 1 H), 7.21 (s, 1 H), 7.42 (d, J=2.07 Hz, 2 H), 9.45 (s, 1H).

Example 6

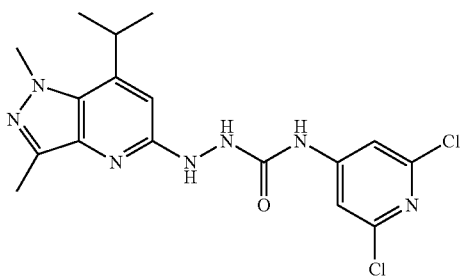

Synthesis of N-(2,6-dichloropyridin-4-yl)-2-(7-isopropyl-1,3-dimethyl-1H-pyrazolo[4,3-b]pyridin-5-yl)hydrazinecarboxamide The title compound was generated from (7-isopropyl-1,3-dimethyl-1H-pyrazolo[4,3-b]pyridin-5-yl)-hydrazine prepared above and commercially available 2,6-dichloro-4-isocyanatopyridine according to General procedure B described above.

N-(2,6-Dichloropyridin-4-yl)-2-(7-isopropyl-1,3-dimethyl-1H-pyrazolo[4,3-b]pyridin-5-yl)hydrazinecarboxamide: The title compound was obtained from 3,5-dichlorophenyl isocyanate (commercially available, 124 mg, 0.66 mmol), 5-hydrazinyl-7-isopropyl-1,3-dimethyl-1H-pyrazolo[4,3-b]pyridine (prepared above, 120 mg, 0.55 mmol) according to the protocols as outlined in general procedure B above. Spectroscopic Data: $^1$H NMR (300 MHz, CD$_3$OD) δ ppm 1.37 (d, J=6.73 Hz, 6 H), 2.44 (s, 3 H), 3.68 (hept, J=6.73 Hz, 1 H), 4.14 (s, 3 H), 6.82 (s, 1 H), 7.63 (s, 2 H).

Example 7

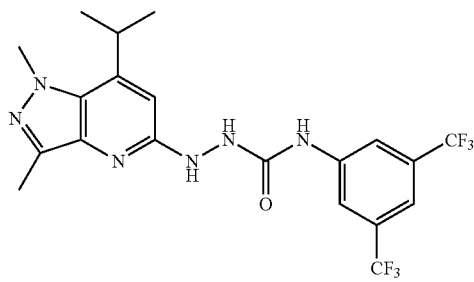 [SMILES: Cc1nn(C)c2c(C(C)C)cc(NNC(=O)Nc3cc(C(F)(F)F)cc(C(F)(F)F)c3)nc12]

Synthesis of N-(3,5-bis(trifluoromethyl)phenyl)-2-(7-isopropyl-1,3-dimethyl-1H-pyrazolo[4,3-b]pyridin-5-yl)hydrazinecarboxamide The title compound was generated from 5-hydrazinyl-7-isopropyl-1,3-dimethyl-1H-pyrazolo[4,3-b]pyridine prepared above and commercially available 4-isocyanato-2,6-bis(trifluoromethyl)pyridine according to General procedure B described above.

N-(3,5-Bis(trifluoromethyl)phenyl)-2-(7-isopropyl-1,3-dimethyl-1H-pyrazolo[4,3-b]pyridin-5-yl)hydrazinecarboxamide: The title compound was obtained from 4-isocyanato-2,6-bis(trifluoromethyl)pyridine (commercially available, 117 mg, 0.44 mmol), 5-hydrazinyl-7-isopropyl-1,3-dimethyl-1H-pyrazolo[4,3-b]pyridine (prepared above, 80 mg, 0.36 mmol) according to the protocols as outlined in general procedure B above. Spectroscopic Data: $^1$H NMR (300 MHz, CD$_3$OD) δ ppm 1.38 (d, J=6.73 Hz, 6 H), 2.44 (s, 3 H), 3.68 (hept, J=6.73 Hz, 1 H), 4.14 (s, 3 H), 6.86 (s, 1 H), 7.53 (s, 1 H), 8.19 (s, 2 H).

Example 8

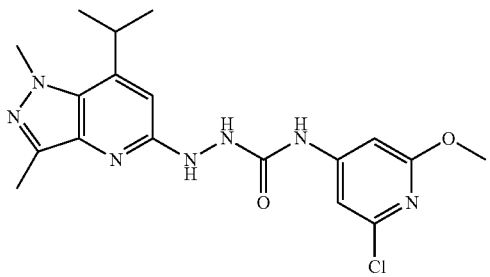 [SMILES: COc1cc(NC(=O)NNc2cc(C(C)C)c3c(n2)c(C)nn3C)cc(Cl)n1]

Synthesis of N-(3-chloro-5-methoxypyridin-4-yl)-2-(7-isopropyl-1,3-dimethyl-1H-pyrazolo[4,3-b]pyridin-5-yl)hydrazinecarboxamide The title compound was generated from (7-isopropyl-1,3-dimethyl-1H-pyrazolo[4,3-b]pyridin-5-yl)-hydrazine prepared above and 2-chloro-6-methoxy-4-isocyanatopyridine according to General procedure B described above. Intermediate 2-chloro-6-methoxy-4-isocyanatopyridine was prepared according to general procedure A and used in situ without further purification.

N-(3-Chloro-5-methoxypyridin-4-yl)-2-(7-isopropyl-1,3-dimethyl-1H-pyrazolo[4,3-b]pyridin-5-yl)hydrazinecarboxamide: The title compound was obtained from 2-chloro-6-methoxy-4-isocyanato-pyridine (prepared above according to general procedure A, crude), 5-hydrazinyl-7-isopropyl-1,3-dimethyl-1H-pyrazolo[4,3-b]pyridine (prepared above, 140 mg, 0.64 mmol) according to the protocols as outlined in general procedure B above. Spectroscopic Data: $^1$H NMR (300 MHz, CD$_3$OD) δ ppm 1.37 (d, J=6.80 Hz, 6 H), 2.44 (s, 3 H), 3.69 (hept, J=6.80 Hz, 1 H), 3.38 (s, 3 H), 4.14 (s, 3 H), 6.83 (s, 1 H), 6.95 (s, 1 H), 7.01 (s, 1 H).

Example 9

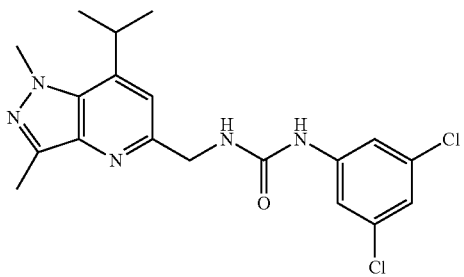

Synthesis of 1-(2,6-dichlorophenyl)-3-((7-isopropyl-1,3-dimethyl-1H-pyrazolo[4,3-b]pyridin-5-yl)methyl)urea The title compound was generated from (7-isopropyl-1,3-dimethyl-1H-pyrazolo[4,3-b]pyridin-5-yl)methanamine prepared above and commercially available 1,3-dichloro-5-isocyanatobenzene according to General procedure B described above.

1-(3,5-Dichlorophenyl)-3-((7-isopropyl-1,3-dimethyl-1H-pyrazolo[4,3-b]pyridin-5-yl)methyl)urea: The title compound was obtained from 1,3-dichloro-5-isocyanatobenzene (commercially available, 188 mg, 1.0 mmol), (7-isopropyl-1,3-dimethyl-1H-pyrazolo[4,3-b]pyridin-5-yl)methanamine (prepared above, 200 mg, 0.92 mmol) according to the protocols as outlined in general procedure B above. Spectroscopic Data: $^1$H NMR (300 MHz, CD$_3$OD) δ ppm 1.40 (d, J=6.73 Hz, 6 H), 2.57 (s, 3 H), 3.76 (hept, J=6.73 Hz, 1 H), 4.21 (s, 3 H), 4.59 (s, 2 H), 6.99 (dd, J=1.76 Hz, 1 H), 7.34 (s, 1 H), 7.43 (d, J=1.76 Hz, 2 H).

Example 10

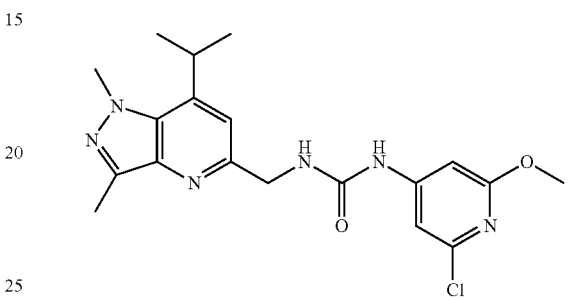

Synthesis of 1-(2-chloro-6-methoxypyridin-4-yl)-3-((7-isopropyl-1,3-dimethyl-1H-pyrazolo[4,3-b]pyridin-5-yl)methyl)urea The title compound was generated from (7-isopropyl-1,3-dimethyl-1H-pyrazolo[4,3-b]pyridin-5-yl)methanamine prepared above and 2-chloro-4-isocyanato-6-methoxypyridine (prepared according to general procedure A described above) according to General procedure B described above.

1-(2-Chloro-6-methoxypyridin-4-yl)-3-((7-isopropyl-1,3-dimethyl-1H-pyrazolo[4,3-h]pyridin-5-yl)methyl)urea: The title compound was obtained from 2-chloro-4-isocyanato-6-methoxypyridine (prepared above, crude, 1.0 mmol), (7-isopropyl-1,3-dimethyl-1H-pyrazolo[4,3-b]pyridin-5-yl)methanamine (prepared above, 200 mg, 0.92 mmol) according to the protocols as outlined in general procedure B above. Spectroscopic Data: $^1$H NMR (300 MHz, CD$_3$OD) δ ppm 1.40 (d, J=6.73 Hz, 6 H), 2.57 (s, 3 H), 3.76 (hept, J=6.73 Hz, 1 H), 4.21 (s, 3 H), 4.59 (s, 2 H), 6.82 (d, J=1.76 Hz, 1 H), 7.06 (d, J=1.76 Hz, 1 H), 7.33 (s, 1 H).

Example 11

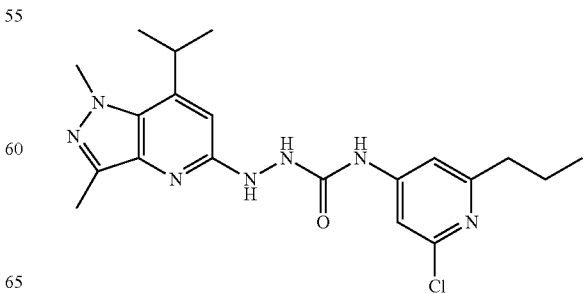

Synthesis of N-(2-chloro-6-propylpyridin-4-yl)-2-(7-isopropyl-1,3-dimethyl-1H-pyrazolo[4,3-b]pyridin-5-yl)hydrazinecarboxamide The title compound was generated from (7-isopropyl-1,3-dimethyl-1H-pyrazolo[4,3-b]pyridin-5-yl)-hydrazine prepared above and 2-chloro-4-isocyanato-6-propylpyridine according to General procedure B described above. Intermediate 2-chloro-4-isocyanato-6-propylpyridine was prepared according to general procedure A and used in situ without further purification.

N-(2-Chloro-6-propylpyridin-4-yl)-2-(7-isopropyl-1,3-dimethyl-1H-pyrazolo[4,3-b]pyridin-5-yl)hydrazinecarboxamide: The title compound was obtained from 2-chloro-4-isocyanato-6-propylpyridine (prepared above), 5-hydrazinyl-7-isopropyl-1,3-dimethyl-1H-pyrazolo[4,3-b]pyridine (prepared above, 200 mg, 0.92 mmol) according to the protocols as outlined in general procedure B above. Spectroscopic Data: $^1$H NMR (300 MHz, CD$_3$OD) δ ppm 0.94 (t, J=7.32 Hz, 3 H), 1.37 (d, J=6.73 Hz, 6 H), 1.69 (m, 2 H), 2.44 (s, 3 H), 2.61 (t, J=7.68 Hz, 2 H), 3.68 (hept, J=6.73 Hz, 1 H), 4.14 (s, 3 H), 6.84 (s, 1 H), 7.37 (s, 1 H), 7.57 (s, 1 H).

Example 12

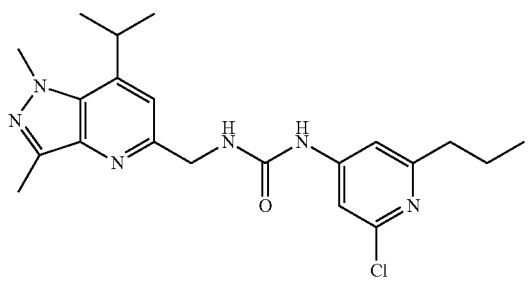

Synthesis of 1-(2-chloro-6-propylpyridin-4-yl)-3-((7-isopropyl-1,3-dimethyl-1H-pyrazolo[4,3-b]pyridin-5-yl)methyl)urea The title compound was generated from (7-isopropyl-1,3-dimethyl-1H-pyrazolo[4,3-b]pyridin-5-yl)methanamine prepared above and 2-chloro-4-isocyanato-6-propylpyridine according to General procedure B described above. Intermediate 2-chloro-4-isocyanato-6-propylpyridine was prepared according to general procedure A and used in situ without further purification.

1-(2-Chloro-6-propylpyridin-4-yl)-3-((7-isopropyl-1,3-dimethyl-1H-pyrazolo[4,3-b]pyridin-5-yl)methyl)urea: The title compound was obtained from 2-chloro-4-isocyanato-6-propylpyridine (prepared above), (7-isopropyl-1,3-dimethyl-1H-pyrazolo[4,3-b]pyridin-5-yl)methanamine (prepared above, 200 mg, 0.92 mmol) according to the protocols as outlined in general procedure B above. Spectroscopic Data: $^1$H NMR (300 MHz, CD$_3$OD) δ ppm 0.94 (t, J=7.32 Hz, 3 H), 1.37 (d, J=6.73 Hz, 6 H), 1.69 (m, 2 H), 2.44 (s, 3 H), 2.61 (t, J=7.68 Hz, 2 H), 3.68 (hept, J=6.73 Hz, 1 H), 4.14 (s, 3 H), 6.84 (s, 1 H), 7.37 (s, 1 H), 7.57 (s, 1 H).

Example 13

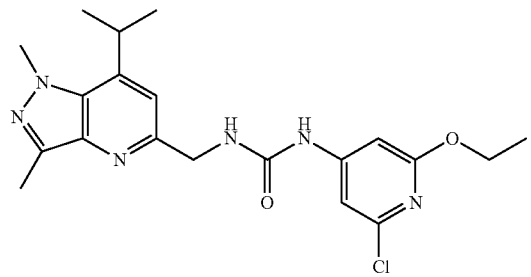 [SMILES: CCOc1cc(NC(=O)NCc2cc(C(C)C)c3c(n2)c(C)nn3C)cc(Cl)n1]

Synthesis of 1-(2-chloro-6-ethoxypyridin-4-yl)-3-((7-isopropyl-1,3-dimethyl-1H-pyrazolo[4,3-b]pyridin-5-yl)methyl)urea The title compound was generated from (7-isopropyl-1,3-dimethyl-1H-pyrazolo[4,3-b]pyridin-5-yl)methanamine prepared above and 2-chloro-6-ethoxy-4-isocyanatopyridine according to General procedure B described above. Intermediate 2-chloro-6-ethoxy-4-isocyanatopyridine was prepared according to general procedure A and used in situ without further purification.

1-(2-Chloro-6-ethoxypyridin-4-yl)-3-((7-isopropyl-1,3-dimethyl-1H-pyrazolo[4,3-h]pyridin-5-yl)methyl)urea: The title compound was obtained from 2-chloro-6-ethoxy-4-isocyanatopyridine (prepared above), (7-isopropyl-1,3-dimethyl-1H-pyrazolo[4,3-b]pyridin-5-yl)methanamine (prepared above, 200 mg, 0.92 mmol) according to the protocols as outlined in general procedure B above. Spectroscopic Data: $^1$H NMR (300 MHz, CD$_3$OD) δ ppm 1.34 (t, J=7.04 Hz, 3 H), 1.39 (d, J=6.73 Hz, 6 H), 2.57 (s, 3 H), 3.76 (hept, J=6.73 Hz, 1 H), 4.21 (s, 3 H), 4.25 (q, J=7.04 Hz, 2 H), 4.59 (s, 2 H), 6.78 (d, J=1.46 Hz, 1 H), 7.04 (d, J=1.46 Hz, 1 H), 7.33 (s, 1 H).

Example 14

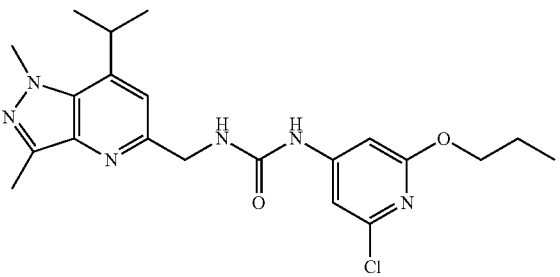 [SMILES: CCCOc1cc(NC(=O)NCc2cc(C(C)C)c3c(n2)c(C)nn3C)cc(Cl)n1]

Synthesis of 1-(2-chloro-6-propoxypyridin-4-yl)-3-((7-isopropyl-1,3-dimethyl-1H-pyrazolo[4,3-b]pyridin-5-yl)methyl)urea The title compound was generated from (7-isopropyl-1,3-dimethyl-1H-pyrazolo[4,3-b]pyridin-5-yl)methanamine prepared above and 2-chloro-4-isocyanato-6-propoxypyridine according to General procedure B described above. Intermediate 2-chloro-4-isocyanato-6-propoxypyridine was prepared according to general procedure A and used in situ without further purification.

1-(2-Chloro-6-propoxypyridin-4-yl)-3-((7-isopropyl-1,3-dimethyl-1H-pyrazolo[4,3-h]pyridin-5-yl)methyl)urea The title compound was obtained from 2-chloro-4-isocyanato-6-propoxypyridine (prepared above), (7-isopropyl-1,3-dimethyl-1H-pyrazolo[4,3-b]pyridin-5-yl)methanamine (prepared above, 180 mg, 0.82 mmol) according to the protocols as outlined in general procedure B above. Spectroscopic Data: $^1$H NMR (300 MHz, CD$_3$OD) δ ppm 1.00 (t, J=7.32 Hz, 3 H), 1.40 (d, J=6.73 Hz, 6 H), 1.75 (m, 2 H), 2.57 (s, 3 H), 3.76 (hept, J=6.73 Hz, 1 H), 4.15 (t, J=6.60 Hz, 2 H), 4.21 (s, 3 H), 4.59 (s, 2 H), 6.78 (d, J=1.46 Hz, 1 H), 7.04 (d, J=1.46 Hz, 1 H), 7.34 (s, 1 H).

Example 15

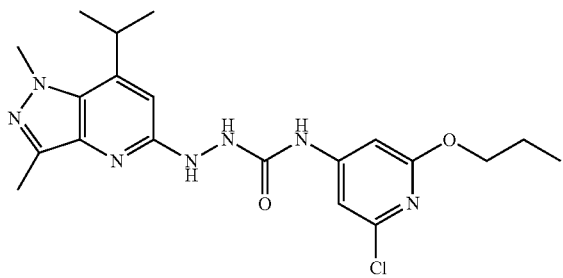

Synthesis of N-(2-chloro-6-propoxypyridin-4-yl)-2-(7-isopropyl-1,3-dimethyl-1H-pyrazolo[4,3-b]pyridin-5-yl)hydrazinecarboxamide The title compound was generated from 5-hydrazinyl-7-isopropyl-1,3-dimethyl-1H-pyrazolo[4,3-b]pyridine prepared above and 2-chloro-4-isocyanato-6-propoxypyridine according to General procedure B described above. Intermediate 2-chloro-4-isocyanato-6-propoxypyridine was prepared according to general procedure A and used in situ without further purification.

N-(3-Chloro-5-propoxyphenyl)-2-(7-isopropyl-1,3-dimethyl-1H-pyrazolo[4,3-h]pyridin-5-yl)hydrazinecarboxamide: The title compound was obtained from 2-chloro-4-isocyanato-6-propoxypyridine (prepared above according to general procedure A, crude), 5-hydrazinyl-7-isopropyl-1,3-dimethyl-1H-pyrazolo[4,3-b]pyridine (prepared above, 160 mg, 0.73 mmol) according to the protocols as outlined in general procedure B above. Spectroscopic Data: $^1$H NMR (300 MHz, CD$_3$OD) δ ppm 1.00 (t, J=7.34 Hz, 3 H), 1.38 (d, J=6.73 Hz, 6 H), 1.74 (m, 2 H), 2.44 (s, 3 H), 3.67 (hept, J=6.73 Hz, 1 H), 4.12-4.17 (m, 5 H), 6.83 (s, 1 H), 6.94 (s, 1 H), 7.19 (s, 1 H).

Example 16

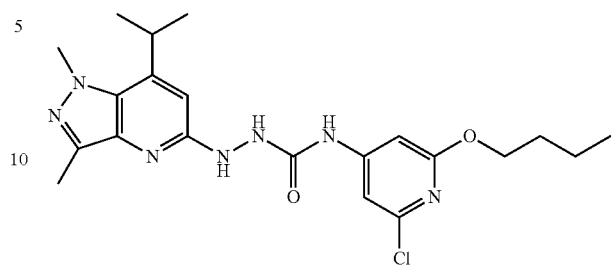

Synthesis of N-(2-butoxy-6-chloropyridin-4-yl)-2-(7-isopropyl-1,3-dimethyl-1H-pyrazolo[4,3-b]pyridin-5-yl)hydrazinecarboxamide The title compound was generated from 5-hydrazinyl-7-isopropyl-1,3-dimethyl-1H-pyrazolo[4,3-b]pyridine prepared above and 2-butoxy-6-chloro-4-isocyanatopyridine according to General procedure B described above. Intermediate 2-butoxy-6-chloro-4-isocyanatopyridine was prepared according to general procedure A and used in situ without further purification.

N-(2-Butoxy-6-chloropyridin-4-yl)-2-(7-isopropyl-1,3-dimethyl-1H-pyrazolo[4,3-b]pyridin-5-yl)hydrazinecarboxamide: The title compound was obtained from 2-butoxy-6-chloro-4-isocyanatopyridine (prepared above according to general procedure A, crude), 5-hydrazinyl-7-isopropyl-1,3-dimethyl-1H-pyrazolo[4,3-b]pyridine (prepared above, 160 mg, 0.73 mmol) according to the protocols as outlined in general procedure B above. Spectroscopic Data: $^1$H NMR (300 MHz, CD$_3$OD) δ ppm 0.97 (t, J=7.34 Hz, 3 H), 1.38 (d, J=6.73 Hz, 6 H), 1.46 (m, 2 H), 1.71 (m, 2 H), 2.44 (s, 3 H), 3.68 (hept, J=6.73 Hz, 1 H), 4.14 (s, 3 H), 4.20 (t, J=6.44 Hz, 2 H), 6.83 (s, 1 H), 6.93 (s, 1 H), 7.19 (s, 1 H).

Example 17

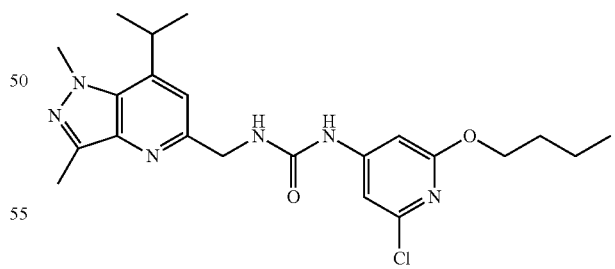

Synthesis of 1-(2-butoxy-6-chloropyridin-4-yl)-3-((7-isopropyl-1,3-dimethyl-1H-pyrazolo[4,3-b]pyridin-5-yl)methyl)urea The title compound was generated from (7-isopropyl-1,3-dimethyl-1H-pyrazolo[4,3-b]pyridin-5-yl)methanamine prepared above and 2-butoxy-6-chloro-4-isocyanatopyridine according to General procedure B described above. Intermediate 2-butoxy-6-chloro-4-isocyanatopyridine was prepared according to general procedure A and used in situ without further purification.

1-(2-Butoxy-6-chloropyridin-4-yl)-3-((7-isopropyl-1,3-dimethyl-1H-pyrazolo[4,3-b]pyridin-5-yl)methyl)urea: The title compound was obtained from 2-chloro-4-isocyanato-6-propoxypyridine (prepared above), (7-isopropyl-1,3-dimethyl-1H-pyrazolo[4,3-b]pyridin-5-yl)methanamine (prepared above, 170 mg, 0.78 mmol) according to the protocols as outlined in general procedure B above. Spectroscopic Data: $^1$H NMR (300 MHz, CD$_3$OD) δ ppm 0.97 (t, J=7.32 Hz, 3 H), 1.40 (d, J=6.73 Hz, 6 H), 1.50 (m, 2 H), 1.72 (m, 2 H), 2.57 (s, 3 H), 3.76 (hept, J=6.73 Hz, 1 H), 4.20 (t, J=6.44 Hz, 2 H), 4.21 (s, 3 H), 4.59 (s, 2 H), 6.80 (d, J=1.46 Hz, 1 H), 7.04 (d, J=1.46 Hz, 1 H), 7.34 (s, 1 H).

Example 18

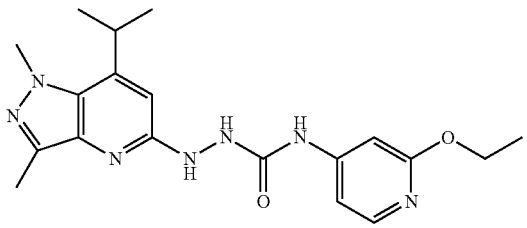 [SMILES: CCOc1cc(NC(=O)NNc2cc(C(C)C)c3c(n2)c(C)nn3C)ccn1]

Synthesis of N-(2-ethoxypyridin-4-yl)-2-(7-isopropyl-1,3-dimethyl-1H-pyrazolo[4,3-b]pyridin-5-yl)hydrazinecarboxamide The title compound was generated from 5-hydrazinyl-7-isopropyl-1,3-dimethyl-1H-pyrazolo[4,3-b]pyridine prepared above and 2-ethoxy-4-isocyanatopyridine according to General procedure B described above. Intermediate 2-ethoxy-4-isocyanatopyridine was prepared according to general procedure A and used in situ without further purification.

N-(2-Ethoxypyridin-4-yl)-2-(7-isopropyl-1,3-dimethyl-1H-pyrazolo[4,3-b]pyridin-5-yl)hydrazinecarboxamide: The title compound was obtained from 2-ethoxy-4-isocyanatopyridine (prepared above according to general procedure A, crude), 5-hydrazinyl-7-isopropyl-1,3-dimethyl-1H-pyrazolo[4,3-b]pyridine (prepared above, 160 mg, 0.73 mmol) according to the protocols as outlined in general procedure B above. Spectroscopic Data: $^1$H NMR (300 MHz, CD$_3$OD) δ ppm 1.34 (t, J=7.04 Hz, 3 H), 1.38 (d, J=6.73 Hz, 6 H), 2.44 (s, 3 H), 3.69 (hept, J=6.73 Hz, 1 H), 4.14 (s, 3 H), 4.24 (q, J=7.04 Hz, 2 H), 6.84 (s, 1 H), 7.04-7.07 (m, 2 H), 7.86 (d, J=6.00 Hz, 1 H).

Example 19

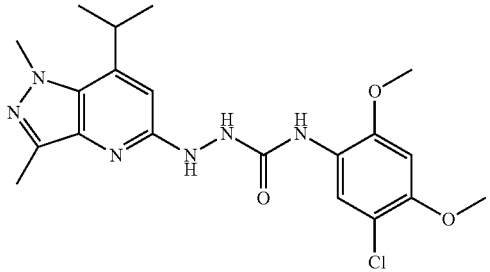 [SMILES: COc1cc(OC)c(NC(=O)NNc2cc(C(C)C)c3c(n2)c(C)nn3C)cc1Cl]

Synthesis of N-(5-chloro-2,4-dimethoxyphenyl)-2-(7-isopropyl-1,3-dimethyl-1H-pyrazolo[4,3-b]pyridin-5-yl)hydrazinecarboxamide The title compound was generated from 5-hydrazinyl-7-isopropyl-1,3-dimethyl-1H-pyrazolo[4,3-b]pyridine prepared above and commercially available 1-chloro-5-isocyanato-2,4-dimethoxybenzene according to General procedure B described above.

N-(5-Chloro-2,4-dimethylphenyl)-2-(7-isopropyl-1,3-dimethyl-1H-pyrazolo[4,3-b]pyridin-5-yl)hydrazinecarboxamide: The title compound was obtained from 1-chloro-5-isocyanato-2,4-dimethoxybenzene and 5-hydrazinyl-7-isopropyl-1,3-dimethyl-1H-pyrazolo[4,3-b]pyridine (prepared above, 160 mg, 0.73 mmol) according to the protocols as outlined in general procedure B above. Spectroscopic Data: $^1$H NMR (300 MHz, CD$_3$OD) δ ppm 1.37 (d, J=6.73 Hz, 6 H), 2.45 (s, 3 H), 3.68 (hept, J=6.73 Hz, 1 H), 3.82 (s, 3 H), 3.85 (s, 3 H), 4.14 (s, 3 H), 6.70 (s, 1 H), 6.86 (s, 1 H), 8.01 (s, 1 H).

Example 20

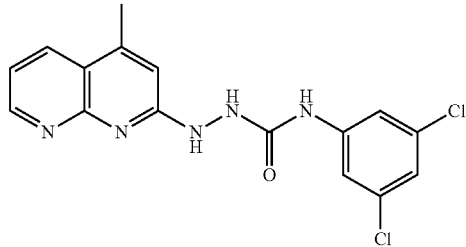 [SMILES: Cc1cc(NNC(=O)Nc2cc(Cl)cc(Cl)c2)nc2ncccc12]

Synthesis of N-(3,5-dichlorophenyl)-2-(4-methyl-1,8-naphthyridin-2-yl)hydrazinecarboxamide The title compound was generated from N-(pyridin-2-yl)pivalamide according to the chemistry described in the following scheme. The intermediates were separated and characterized.

Scheme 1

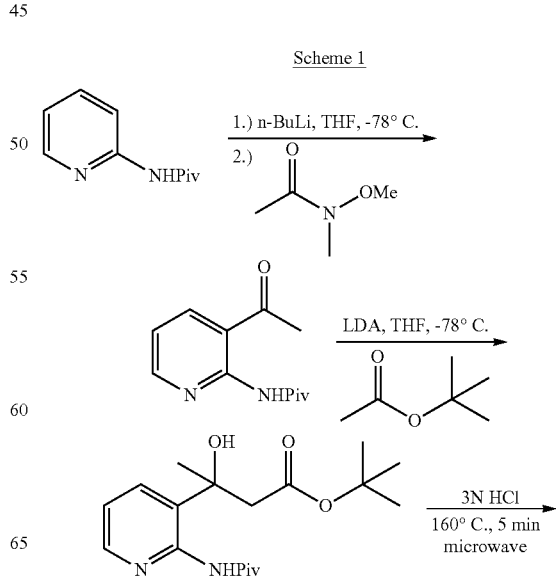

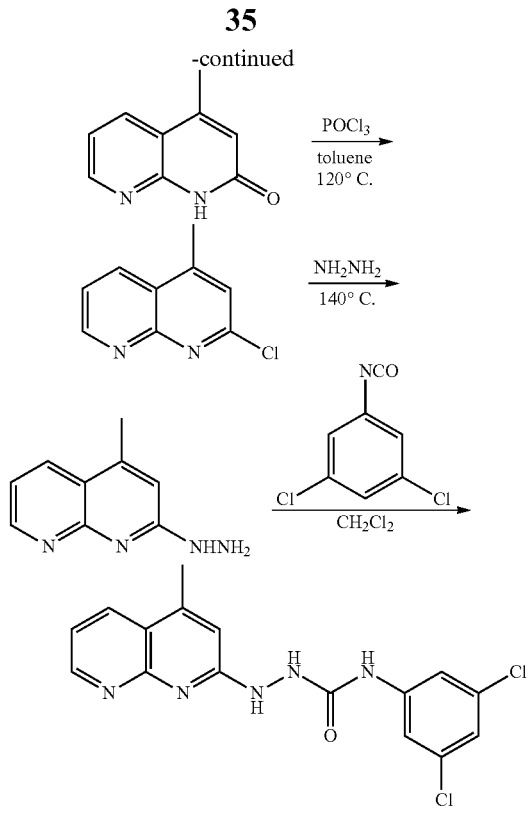

N-(3-Acetylpyridin-2-yl)pivalamide: To a solution of N-(pyridin-2-yl)pivalamide (2.0 g, 11.22 mmoles) in THF at −78° C. was added 9.4 mL (2.1 eq) of n-BuLi. The resulting mixture was stirred at 0° C. for 3 hours. The reaction mixture was then cooled to −78° C. after which N-methoxy-N-methylacetamide (1.2 g, 1.1 eq) was added as a solution in THF. The resulting mixture was stirred at room temperature for 2 hours. It was then quenched into ice-$H_2O$. The resulting mixture was extracted with $CH_2Cl_2$ (3×20 mL) and the combined organic extracts were washed with $H_2O$ (2×20 mL), brine (1x 20 mL), then dried over $MgSO_4$. Concentration and purification by MPLC gave N-(3-acetylpyridin-2-yl)pivalamide (1.62 g, 65%). Spectroscopic data: $^1$H NMR (300 MHz, $CDCl_3$) δ ppm 1.36 (s, 9 H) 2.65 (s, 3 H) 7.09 (dd, J=7.76, 4.83 Hz, 1 H) 8.17 (dd, J=7.76, 1.90 Hz, 1 H) 8.64 (dd, J=4.69, 2.05 Hz, 1 H) 11.49 (br. s., 1 H).

tert-Butyl 3-hydroxy-3-(2-pivalamidopyridin-3-yl)butanoate: To a solution of 9.5 mL (2.1 eq) of LDA in 15 mL THF at −78° C. was added 2.0 mL of t-butyl acetate (2.1 eq.). The resulting mixture was stirred at −78° C. for 30 minutes after which a solution of N-(3-acetylpyridin-2-yl)pivalamide (1.52 g, 6.90 mmol) in THF was added in a dropwise fashion. The resulting reaction mixture was then stirred at −78° C. for 30 minutes and was brought up to room temperature. The reaction mixture was then quenched with saturated $NH_4Cl$. The resulting mixture was extracted with EtOAc (3×20 mL) and the combined organic extracts were washed with $H_2O$ (2×20 mL), brine (1x 20 mL), dried over $MgSO_4$ and concentrated to give the title compound (1.40 g, 61%). Spectroscopic data: $^1$H NMR (300 MHz, $CDCl_3$) δ ppm 1.33 (s, 9 H) 1.44 (s, 9 H) 1.58 (s, 3 H) 2.65 (d, J=16.70 Hz, 1 H) 3.06 (d, J=16.70 Hz, 1 H) 5.54 (s, 1 H) 6.96 (dd, J=7.76, 4.83 Hz, 1 H) 7.43 (dd, J=7.91, 1.76 Hz, 1 H) 8.45 (dd, J=4.98, 1.76 Hz, 1 H) 10.29 (s, 1 H).

4-Methyl-1,8-naphthyridin-2(1 H)-one: A solution of 1.3 g of tert-butyl 3-hydroxy-3-(2-pivalamidopyridin-3-yl)butanoate (3.9 mmol) in 2 mL 3N HCl was microwaved at 160° C. for 5 minutes. The resulting mixture was washed with $Et_2O$ (2×10 mL). The aqueous layer was basified using saturated $K_2CO_3$. The precipitate formed was filtered and washed with water to give 440 mg (71%) of the desired title compound. Spectroscopic data: $^1$H NMR (300 MHz, DMSO-$d_6$) δ ppm 2.40 (d, J=1.17 Hz, 3 H) 6.43 (s, 1 H) 7.24 (dd, J=7.91, 4.69 Hz, 1 H) 8.12 (dd, J=7.91, 1.76 Hz, 1 H) 8.49 (dd, J=4.69, 1.76 Hz, 1 H) 11.92 (br. s., 1 H).

2-Chloro-4-methyl-1,8-naphthyridine To a solution of 4-methyl-1,8-naphthyridin-2(1 H)-one (440 mg, 2.75 mmol) in toluene was added 302 uL of $POCl_3$ (1.2 eq). The resulting mixture was refluxed at 120° C. for 3 hours. After cooling to room temperature the reaction mixture was quenched into ice-$H_2O$ and extracted with EtOAc (3×10 mL). The combined organic extracts was washed with $H_2O$ (2×15 mL), brine (1×20 mL), and then dried over $MgSO_4$. Concentration and purification by MPLC gave the desired 2-chloro-4-methyl-1,8-naphthyridine (330 mg, 67%). Spectroscopic data: $^1$H NMR (300 MHz, $CDCl_3$) δ ppm 2.72 (s, 3 H) 7.35 (d, J=1.17 Hz, 1 H) 7.53 (dd, J=8.20, 4.40 Hz, 1 H) 8.36 (dd, J=8.35, 1.90 Hz, 1 H) 9.10 (dd, 1 H).

2-Hydrazinyl-4-methyl-1,8-naphthyridine: A solution of 2-chloro-4-methyl-1,8-naphthyridine (330 mg, 1.8 mmol) in $NH_2NH_2$ was refluxed at 130° C. for 2 hours. The reaction mixture was cooled to room temperature, then excess $NH_2NH_2$ was removed on the rotary evaporator. The residue was taken up in 20 mL of $CH_2Cl_2$. The mixture was washed with saturated $NaHCO_3$ (3×15 mL), brine (1x 20 mL), and then dried over $MgSO_4$ and concentrated. The residue was washed with hexane to give 2-hydrazinyl-4-methyl-1,8-naphthyridine. Spectroscopic data: $^1$H NMR (300 MHz, $CDCl_3$) δ ppm 2.56 (s, 3 H) 6.66 (s, 1 H) 7.22 (dd, J=7.91, 4.40 Hz, 1 H) 8.11 (dd, J=8.06, 1.90 Hz, 1 H) 8.82 (dd, 1 H).

N-(3,5-Dichlorophenyl)-2-(4-methyl-1,8-naphthyridin-2-yl)hydrazinecarboxamide: To a solution of 2-hydrazinyl-4-methyl-1,8-naphthyridine prepared above (84 mg, 0.482 mmol) in $CH_2Cl_2$ was added 3,5-dichlorophenyl isocyanate (91 mg, 1.0 eq). The resulting mixture was stirred at room temperature overnight. The resulting precipitate was filtered off and washed with EtOAc to give the desired title compound. Spectroscopic data: $^1$H NMR (300 MHz, DMSO-$d_6$) δ ppm 2.51 (s, 3 H) 6.78 (s, 1 H) 7.05 (t, J=1.90 Hz, 1 H) 7.23 (dd, J=7.91, 4.40 Hz, 1 H) 7.61 (br. s., 2 H) 8.22 (dd, J=8.06, 1.90 Hz, 1 H) 8.57 (br. s., 1 H) 8.68 (dd, J=4.40, 1.76 Hz, 1 H) 8.98 (s, 1 H) 9.22 (br. s., 1 H).

Example 21

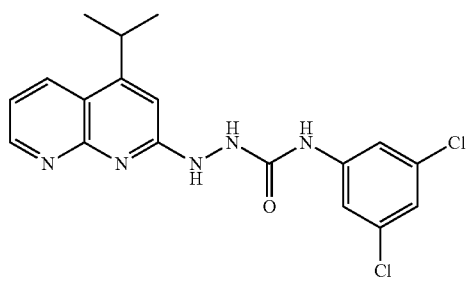

Synthesis of N-(3,5-dichlorophenyl)-2-(4-isopropyl-1,8-naphthyridin-2-yl)hydrazinecarboxamide The title compound was generated from N-(3-isobutyrylpyridin-2-yl)pivalamide according to the chemistry described in scheme 1 described above. The intermediates were separated and characterized.

N-(3-Isobutyrylpyridin-2-yl)pivalamide: A solution of N-(pyridin-2-yl)pivalamide (3.20 g, 18.0 mmol), n-BuLi (15.00 mL, 2.1 eq.) and N-methoxy-N-methylisobutyramide (2.60 g, 1.1 eq) were reacted as outlined in Scheme 1 to give 3.10 g (69%) of N-(3-isobutyrylpyridin-2-yl)pivalamide. Spectroscopic data: $^1$H NMR (300 MHz, CDCl$_3$) δ ppm 1.21 (d, J=7.03 Hz, 6 H) 1.35 (s, 9 H) 3.55 (dt, J=13.70, 6.78 Hz, 1 H) 7.08 (dd, J=7.91, 4.69 Hz, 1 H) 8.19 (dd, J=8.20, 2.05 Hz, 1 H) 8.63 (dd, J=4.83, 1.90 Hz, 1 H) 11.51 (br. s., 1 H).

tert-Butyl 3-hydroxy-4-methyl-3-(2-pivalamidopyridin-3-yl)pentanoate: A solution of N-(3-isobutyrylpyridin-2-yl)pivalamide (3.10 g, 12.5 mmol), LDA (1.5 M, 17.50 mL, 2.1 eq) and t-butyl acetate (3.5 mL, 2.1 eq) were reacted as outlined in Scheme 1 to give tert-butyl 3-hydroxy-4-methyl-3-(2-pivalamidopyridin-3-yl)pentanoate which was used in the next step without further purification.

4-Isopropyl-1,8-naphthyridin-2(1 H)-one: A solution of tert-butyl 3-hydroxy-4-methyl-3-(2-pivalamidopyridin-3-yl)pentanoate (3.78 g, 10.4 mmol) in 12.0 mL 3N HCl were reacted as outlined in Scheme 1 to give the desired 4-isopropyl-1,8-naphthyridin-2(1 H)-one (800 mg, 41%). Spectroscopic data: $^1$H NMR (300 MHz, CDCl$_3$) δ ppm 1.34 (d, J=7.03 Hz, 6 H) 3.34 (quin, J=6.81 Hz, 1 H) 6.66 (s, 1 H) 7.23 (dd, J=12.31, 4.10 Hz, 2 H) 8.09 (dd, J=8.06, 1.61 Hz, 1 H) 8.71 (dd, J=4.69, 1.47 Hz, 1 H) 11.98 (br. s., 1 H).

2-Chloro-4-isopropyl-1,8-naphthyridine: A solution of 4-isopropyl-1,8-naphthyridin-2(1 H)-one (800 mg, 4.3 mmol) and 475 L of POCl$_3$ in toluene were reacted as outlined in Scheme 1 to give the desired 2-chloro-4-isopropyl-1,8-naphthyridine (690 mg, 79%). Spectroscopic data: $^1$H NMR (300 MHz, CDCl$_3$) δ ppm 1.41 (d, J=6.74 Hz, 6 H) 3.68 (dq, J=7.03, 6.84 Hz, 1 H) 7.38 (s, 1 H) 7.52 (dd, J=8.35, 4.25 Hz, 1 H) 8.44 (dd, J=8.50, 2.05 Hz, 1 H) 9.09 (dd, 1 H).

2-Hydrazinyl-4-isopropyl-1,8-naphthyridine: A solution of chloro-4-isopropyl-1,8-naphthyridine (690 mg, 3.4 mmol) in NH$_2$NH$_2$ was reacted as outlined in Scheme 1 above to give the desired title compound (620 mg, 92%). Spectroscopic data: $^1$H NMR (300 MHz, CDCl$_3$) δ ppm 1.35 (d, J=6.74 Hz, 6 H) 3.45-3.59 (m, 1 H) 6.70 (br. s., 1 H) 7.21 (dd, J=8.06, 4.54 Hz, 1 H) 8.19 (d, J=7.62 Hz, 1H) 8.79 (br. s., 1 H).

N-(3,5-Dichlorophenyl)-2-(4-isopropyl-1,8-naphthyridin-2-yl)hydrazinecarboxamide: A 100 mg (0.5 mmol) sample of 2-hydrazinyl-4-isopropyl-1,8-naphthyridine and 94 mg (1.0 eq) of 3,5-dichlorophenyl isocyanate were reacted as outlined in Scheme 1 above to give the desired title compound. Spectroscopic data: $^1$H NMR (300 MHz, DMSO-d$_6$) δ ppm 1.23 (d, J=6.74 Hz, 6 H) 3.56 (d, J=6.74 Hz, 1 H) 6.82 (s, 1 H) 7.04 (t, J=1.76 Hz, 1 H) 7.23 (dd, J=8.20, 4.40 Hz, 1 H) 7.59 (br. s., 2 H) 8.31 (d, J=1.47 Hz, 1 H) 8.54 (br. s., 1 H) 8.66 (d, J=1.17 Hz, 1 H) 8.99 (br. s., 1 H) 9.25 (br. s., 1 H).

Example 22

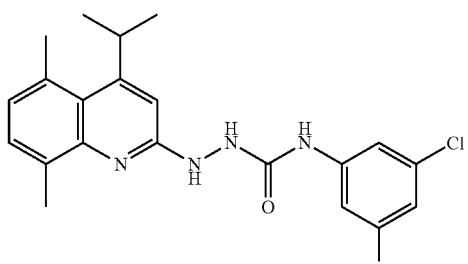

Synthesis of N-(3,5-dichlorophenyl)-2-(4-isopropyl-5,8-dimethylquinolin-2-yl)hydrazinecarboxamide The title compound was generated from 2,5-dimethylaniline according to the chemistry described in the following scheme (Scheme 2). The intermediates were separated and characterized.

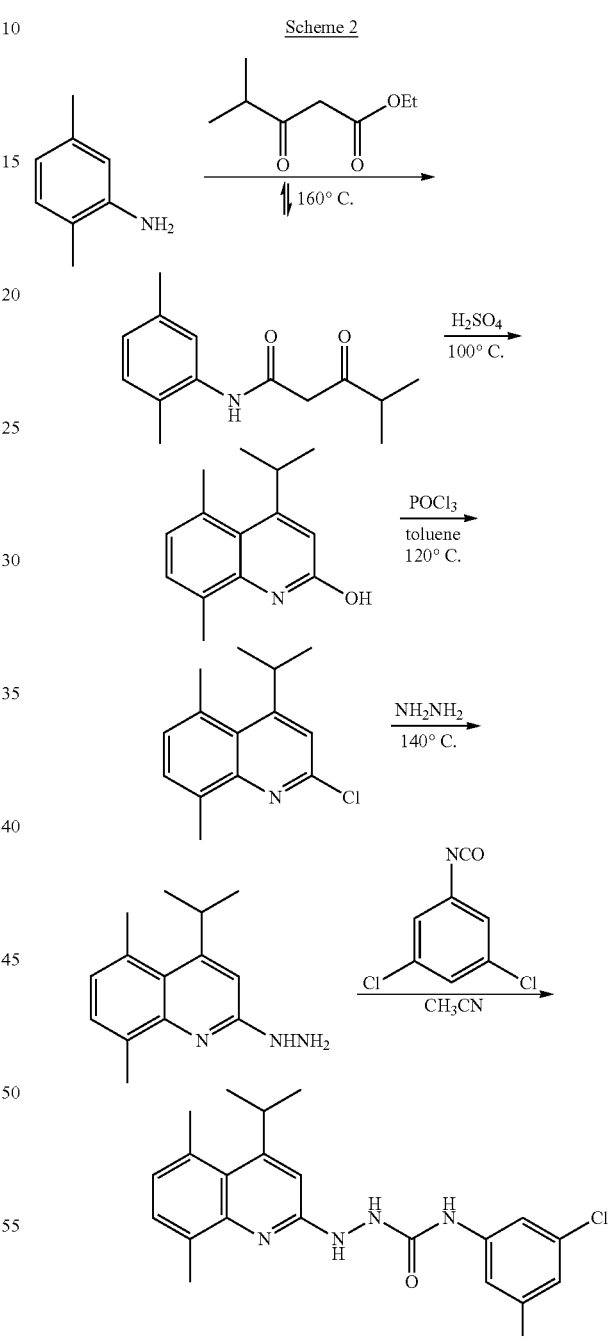

N-(2,5-Dimethylphenyl)-4-methyl-3-oxopentanamide: A mixture of 2,5-dimethylaniline (7.70 g, 63.54 mmol) and ethyl 4-methyl-3-oxopentanoate (10.00 g, 1.0 eq) were refluxed at 160° C. overnight. After the reaction mixture was cooled to room temperature, it was triturated with hexane. The resulting precipitate was filtered and dried under high vacuum to yield the desired N-(2,5-dimethylphenyl)-4-methyl-3-oxopentanamide. Spectroscopic data: $^1$H NMR (300 MHz, CDCl$_3$) δ ppm 1.18 (d, J=7.03 Hz, 6 H) 2.30 (d, J=7.62 Hz, 6 H) 2.66-2.85 (m, 1 H) 3.64 (s, 2 H) 6.87 (d, J=8.50 Hz, 1 H) 7.06 (d, J=7.62 Hz, 1 H) 7.77 (s, 1 H) 9.13 (br. s., 1 H).

4-Isopropyl-5,8-dimethylquinolin-2-ol: A sample of N-(2,5-dimethylphenyl)-4-methyl-3-oxopentanamide and 10.0 mL of H$_2$SO$_4$ was reacted at 100° C. for 1 hour. After the reaction was cooled to room temperature it was quenched into ice-H$_2$O. The resulting mixture was extracted with CH$_2$Cl$_2$ (3×20 mL). The combined organic extracts were washed with saturated NaHCO$_3$ (3×15 mL), brine (1x 20 mL), dried over MgSO$_4$ and concentrated. The residue was recrystallized in EtOAc to give 1.30 g of the desired 4-isopropyl-5,8-dimethylquinolin-2-ol. Spectroscopic data: $^1$H NMR (300 MHz, CDCl$_3$) δ ppm 1.29 (d, J=6.45 Hz, 6 H) 2.41 (s, 3 H) 2.77 (s, 3 H) 3.84 (quin, J=6.59 Hz, 1 H) 6.67 (s, 1 H) 6.93 (d, J=7.62 Hz, 1 H) 7.19 (d, J=7.62 Hz, 1 H) 8.81 (br. s., 1 H).

2-Chloro-4-isopropyl-5,8-dimethylquinoline: A solution of 4-isopropyl-5,8-dimethylquinolin-2-ol (1.30 g, 6.05 mmol), 700 L (1.2 eq) of POCl$_3$ in toluene were reacted as outlined in Scheme 1 above to yield 1.00 g of 2-chloro-4-isopropyl-5,8-dimethylquinoline (71%). Spectroscopic data: $^1$H NMR (300 MHz, CDCl$_3$) δ ppm 1.34 (d, J=6.74 Hz, 6 H) 2.71 (s, 3 H) 2.87 (s, 3 H) 4.12 (quin, J=6.74 Hz, 1 H) 7.21 (d, J=7.33 Hz, 1 H) 7.32 (s, 1 H) 7.40 (d, J=7.33 Hz, 1 H).

2-Hydrazinyl-4-isopropyl-5,8-dimethylquinoline: A solution of 2-chloro-4-isopropyl-5,8-dimethylquinoline (1.00 g, 4.3 mmol) in NH$_2$NH$_2$ was reacted as outlined in Scheme 1 above to give the title compound. Spectroscopic data: $^1$H NMR (300 MHz, CDCl$_3$) δ ppm 1.30 (d, J=6.74 Hz, 6 H) 2.64 (s, 3 H) 2.82 (s, 3 H) 3.95-4.10 (m, 1 H) 6.72 (s, 1 H) 6.98 (d, J=7.33 Hz, 1 H) 7.30 (d, J=7.33 Hz, 1 H).

N-(3,5-Dichlorophenyl)-2-(4-isopropyl-5,8-dimethylquinolin-2-yl)hydrazinecarboxamide: A solution of 2-hydrazinyl-4-isopropyl-5,8-dimethylquinoline (100 mg, 0.44 mmol) and 82 mg (1.0 eq) of 3,5-dichlorophenyl isocyanate was reacted as outlined in Scheme 1 above to give the desired title compound. Spectroscopic data: $^1$H NMR (300 MHz, DMSO-d$_6$) δ ppm 1.23 (d, J=6.74 Hz, 6 H) 2.42 (s, 3 H) 2.74 (s, 3 H) 3.88-4.06 (m, 1 H) 6.89 (s, 1 H) 6.94 (d, J=7.33 Hz, 1 H) 7.07 (t, J=1.90 Hz, 1 H) 7.22 (d, J=7.03 Hz, 1 H) 7.65 (br. s., 2 H) 8.27 (br. s., 1 H) 8.58 (s, 1 H) 9.24 (br. s., 1 H).

Example 23

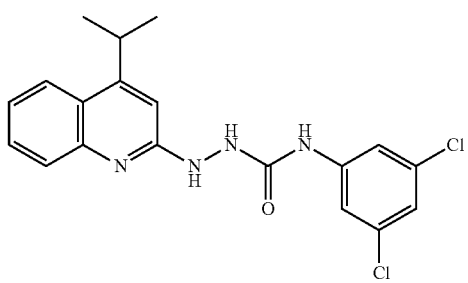 [SMILES: CC(C)c1cc(NNC(=O)Nc2cc(Cl)cc(Cl)c2)nc2ccccc12]

Synthesis of N-(3,5-dichlorophenyl)-2-(4-isopropylquinolin-2-yl)hydrazinecarboxamide The title compound was generated from aniline according to the chemistry described in the Scheme 1 and Scheme 2. The intermediates were separated and characterized.

4-Methyl-3-oxo-N-phenylpentanamide: Aniline (5.80 g, 62.3 mmol) and 10.0 g (1.0 eq.) of ethyl isobutyryl acetate were reacted as outlined in Scheme 2 described above to give 6.70 g (52%) of the desired title compound. Spectroscopic data: $^1$H NMR (300 MHz, CDCl$_3$) δ ppm 1.17 (d, J=7.03 Hz, 6 H) 2.64-2.83 (m, 1 H) 3.61 (s, 2 H) 7.11 (t, J=7.33 Hz, 1 H) 7.32 (t, J=7.91 Hz, 2 H) 7.51-7.59 (m, 2 H) 9.20 (br. s., 1 H).

4-Isopropylquinolin-2-ol: A solution of 4-methyl-3-oxo-N-phenylpentanamide (3.70 g, 18.03 mmol) in 15 mL H$_2$SO$_4$ was reacted as outlined in Scheme 2 above to give 1.95 g (57%) of the desired title compound. Spectroscopic data: $^1$H NMR (300 MHz, CDCl$_3$) δ ppm 1.36 (d, J=6.74 Hz, 6 H) 3.45 (quin, J=6.81 Hz, 1 H) 6.67 (s, 1 H) 7.15-7.32 (m, 1 H) 7.40-7.61 (m, 2 H) 7.79 (d, J=8.50 Hz, 1 H) 12.28 (br. s., 1 H).

2-Chloro-4-isopropylquinoline: 4-Isopropylquinolin-2-ol (1.95 g, 10.43 mmol) and 1.14 mL (1.2 eq) of POCl$_3$ in toluene were reacted as outlined in Scheme 1 above to yield 1.8 g (84%) of the desired title compound. Spectroscopic data: $^1$H NMR (300 MHz, CDCl$_3$) δ ppm 1.40 (d, J=6.74 Hz, 6 H) 3.71 (quin, J=6.81 Hz, 1 H) 7.28 (s, 1 H) 7.48-7.63 (m, 1 H) 7.65-7.78 (m, 1 H) 7.98-8.10 (m, 2 H).

2-Hydrazinyl-4-isopropylquinoline: A solution of 2-chloro-4-isopropylquinoline (1.80 g, 8.8 mmol) in NH$_2$NH$_2$ was reacted as outlined in Scheme 1 above to give the desired title compound. Spectroscopic data: $^1$H NMR (300 MHz, CDCl$_3$) δ ppm 1.41 (d, J=6.74 Hz, 6 H) 3.51-3.76 (m, 1 H) 7.20-7.35 (m, 1 H) 7.44-7.60 (m, 2 H) 7.61-7.79 (m, 1 H) 7.84-8.06 (m, 1 H).

N-(3,5-Dichlorophenyl)-2-(4-isopropylquinolin-2-yl)hydrazinecarboxamide: A solution of 2-hydrazinyl-4-isopropylquinoline (97 mg, 0.48 mmol) and 91 mg (1.0 eq) of 3,5-dichlorophenyl isocyanate was reacted as outlined in Scheme 1 above to give the desired title compound.

Spectroscopic data: $^1$H NMR (300 MHz, DMSO-d$_6$) δ ppm 1.29 (d, J=6.74 Hz, 6 H) 3.53-3.71 (m, 1 H) 6.83 (s, 1 H) 7.09 (t, J=1.90 Hz, 1 H) 7.28 (td, J=7.47, 1.46 Hz, 1 H) 7.45-7.62 (m, 2 H) 7.69 (br. s., 2 H) 7.94 (d, J=7.62 Hz, 1 H) 8.50 (br. s., 1 H) 8.70 (s, 1 H) 9.23 (br. s., 1 H).

Example 24

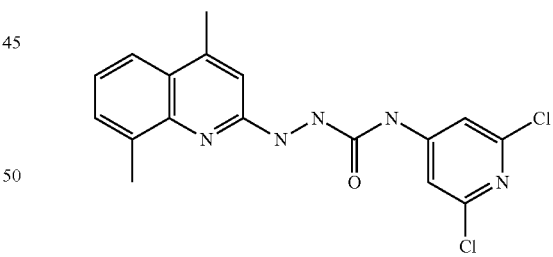

Synthesis of N-(2,6-dichloropyridin-4-yl)-2-(4,8-dimethylquinolin-2-yl)hydrazinecarboxamide The title compound was generated from 2-chloro-4,8-dimethylquinoline according to the chemistry described in Scheme 1 and Scheme 2. The intermediates were separated and characterized.

2-Hydrazinyl-4,8-dimethylquinoline: A solution of 2-chloro-4,8-dimethylquinoline (1.00 g, 5.2 mmoles) in NH$_2$NH$_2$ was reacted as outlined in Scheme 1 above to give the desired title compound which was used in the next step without further purification.

N-(2,6-Dichloropyridin-4-yl)-2-(4,8-dimethylquinolin-2-yl)hydrazinecarboxamide: A solution of 2-hydrazinyl-4,8-dimethylquinoline (110 mg, 0.60 mmol) and 111 mg (1.0 eq) of 2,6-dichloro-4-isocyanatopyridine was reacted as outlined in Scheme 1 above to give the desired title compound. Spectroscopic data: $^1$H NMR (300 MHz, DMSO-$d_6$) δ ppm 2.50 (s, 3 H) 2.56 (s, 3 H) 6.79 (s, 1 H) 7.18 (t, J=7.62 Hz, 1 H) 7.41 (d, J=7.03 Hz, 1 H) 7.70 (d, J=8.20 Hz, 2 H) 8.72 (s, 2 H).

Example 25

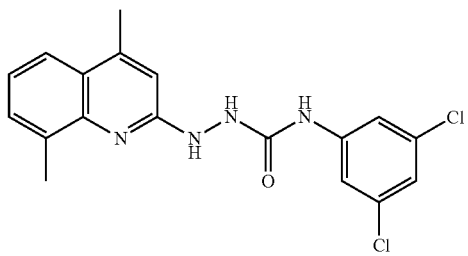 [SMILES: Cc1cc(NNC(=O)Nc2cc(Cl)cc(Cl)c2)nc2c(C)cccc12]

Synthesis of N-(3,5-dichlorophenyl)-2-(4,8-dimethylquinolin-2-yl)hydrazinecarboxamide The title compound was generated from 2-hydrazinyl-4,8-dimethylquinoline according to the chemistry described in Scheme 1. The intermediate 2-hydrazinyl-4,8-dimethylquinoline was prepared according to Scheme 1 and it's characterization was presented earlier (see above).

N-(3,5-Dichlorophenyl)-2-(4,8-dimethylquinolin-2-yl)hydrazinecarboxamide: A solution of 2-hydrazinyl-4,8-dimethylquinoline (100 mg, 0.53 mmol) and 100 mg (1.0 eq) of 1,3-dichloro-5-isocyanatobenzene was reacted as outlined in Scheme 1 above to give the desired title compound. Spectroscopic data: $^1$H NMR (300 MHz, DMSO-$d_6$) δ ppm 2.51 (s, 3 H) 2.55 (s, 3 H) 6.77-6.80 (m, 1 H) 7.09 (t, J=1.76 Hz, 1 H) 7.17 (dd, J=8.20, 7.03 Hz, 1 H) 7.40 (d, J=6.74 Hz, 1 H) 7.65-7.72 (m, 3 H) 8.40 (br. s., 1 H) 8.62 (s, 1 H) 9.25 (br. s., 1 H).

Example 26

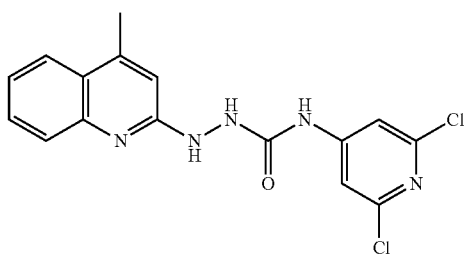 [SMILES: Cc1cc(NNC(=O)Nc2cc(Cl)nc(Cl)c2)nc2ccccc12]

Synthesis of N-(2,6-dichloropyridin-4-yl)-2-(4-methylquinolin-2-yl)hydrazinecarboxamide The title compound was generated from commercially available 2-chloro-4-methylquinoline according to the chemistry described above in Scheme 1. The intermediate 2-hydrazinyl-4-methylquinoline was used in the next step without further purification.

2-Hydrazinyl-4-methylquinoline: A solution of 2-chloro-4-methylquinoline (1.00 g, 5.63 mmol) in NH$_2$NH$_2$ was reacted as outlined in Scheme 1 above to give the title compound which was used in the next step without further purification.

N-(2,6-Dichloropyridin-4-yl)-2-(4-methylquinolin-2-yl)hydrazinecarboxamide: A solution of 2-hydrazinyl-4-methylquinoline (100 mg, 0.58 mmol) and 110 mg (1.0 eq) of 2,6-dichloro-4-isocyanatopyridine was reacted as outlined in Scheme 1 above to give the desired title compound. Spectroscopic data: $^1$H NMR (300 MHz, DMSO-$d_6$) δ ppm 2.57 (s, 3 H) 6.80 (s, 1 H) 7.30 (t, J=7.47 Hz, 1 H) 7.50-7.64 (m, 2 H) 7.87 (d, J=8.20 Hz, 1 H) 8.78 (s, 1 H) 8.91 (br. s., 1 H).

Example 27

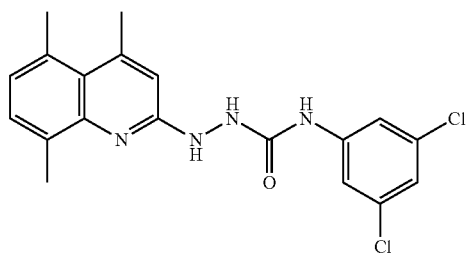 [SMILES: Cc1ccc(C)c2c(C)cc(NNC(=O)Nc3cc(Cl)cc(Cl)c3)nc12]

Synthesis of N-(3,5-dichlorophenyl)-2-(4,5,8-trimethylquinolin-2-yl)hydrazinecarboxamide The title compound was generated from 2,5-dimethylaniline according to the chemistry described in Scheme 1 and Scheme 3 below. The intermediates were separated and characterized.

Scheme 3

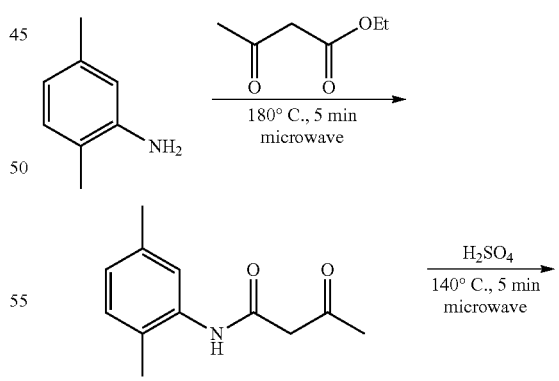

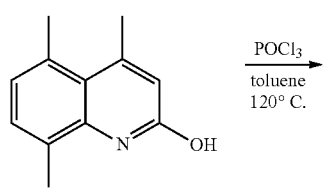

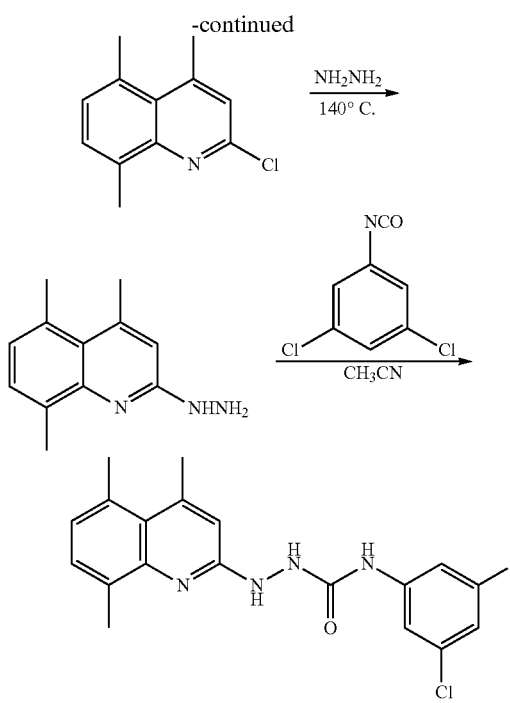

N-(2,5-Dimethylphenyl)-3-oxobutanamide: A mixture of 2,5-dimethylaniline (1.00 g, 8.25 mmol) and ethyl 3-oxobutanoate (1.0 mL, 1.0 eq) was microwaved at 180° C. for 5 minutes. After the reaction mixture was cooled to room temperature, it was triturated with hexane. The resulting precipitate was filtered and dried under high vacuum to yield the desired title compound. Spectroscopic data: $^1$H NMR (300 MHz, CDCl$_3$) δ ppm 2.28 (s, 3 H) 2.32 (s, 3 H) 2.34 (s, 3 H) 3.63 (s, 2 H) 6.88 (d, J=7.62 Hz, 1 H) 7.07 (d, J=7.62 Hz, 1 H) 7.75 (s, 1 H) 9.00-9.12 (m, 1 H).

4,5,8-Trimethylquinolin-2-ol: A 5.50 g (26.8 mmol) sample of N-(2,5-dimethylphenyl)-3-oxobutanamide in 10.0 mL of H$_2$SO$_4$ was microwaved at 140° C. for 5 minutes. After the reaction was cooled to room temperature it was quenched into ice-H$_2$O. The resulting mixture was basified with saturated NaHCO$_3$. The resulting mixture was extracted with CH$_2$Cl$_2$ (3×20 mL) and the combined organic extracts were washed with H$_2$O (1×15 mL), brine (1x 20 mL), dried over MgSO$_4$ and concentrated to give the desired title compound (1.4 g, 28%). Spectroscopic data: $^1$H NMR (300 MHz, CDCl$_3$) δ ppm 2.41 (s, 3 H) 2.69 (d, J=1.17 Hz, 3 H) 2.73 (s, 3 H) 6.48 (s, 1 H) 6.90 (d, J=7.33 Hz, 1 H) 7.19 (d, J=7.62 Hz, 1 H) 8.87 (br. s., 1 H).

2-Chloro-4,5,8-trimethylquinoline: A solution of 4,5,8-trimethylquinolin-2-ol (2.40 g, 12.8 mmol) and 1.4 mL (1.2 eq) of POCl$_3$ in toluene was reacted as outlined in Scheme 1 above to yield the desired title compound (2.2 g, 85%). Spectroscopic data: $^1$H NMR (300 MHz, CDCl$_3$) δ ppm 2.68 (s, 3 H) 2.82 (s, 3 H) 2.85 (s, 3 H) 7.12 (s, 1 H) 7.18 (d, J=7.33 Hz, 1 H) 7.39 (d, 1 H).

2-Hydrazinyl-4,5,8-trimethylquinoline: A solution of 2-chloro-4,5,8-trimethylquinoline (2.2 g, 10.7 mmoles) in NH$_2$NH$_2$ was reacted as outlined in Scheme 1 above to give the desired title compound (830 mg, 38%). Spectroscopic data: $^1$H NMR (300 MHz, CDCl$_3$) δ ppm 2.62 (s, 3 H) 2.78 (s, 6 H) 4.13 (br. s., 2 H) 5.74 (br. s., 1 H) 6.52 (s, 1 H) 6.95 (d, J=7.03 Hz, 1 H) 7.28 (d, 1 H).

N-(3,5-Dichlorophenyl)-2-(4,5,8-trimethylquinolin-2-yl) hydrazinecarboxamide: A solution of 2-hydrazinyl-4,5,8-trimethylquinoline (100 mg, 0.50 mmol) and 93.53 mg (1.0 eq) of 3,5-dichlorophenyl isocyanate was reacted as outlined in Scheme 1 above to give the desired title compound. Spectroscopic data: $^1$H NMR (300 MHz, DMSO-d$_6$) δ ppm 2.43 (s, 3 H) 2.73 (s, 3 H) 2.77 (s, 3 H) 6.69 (s, 1 H) 6.92 (d, J=7.03 Hz, 1 H) 7.09 (t, J=1.90 Hz, 1 H) 7.23 (d, J=7.62 Hz, 1 H) 7.68 (br. s., 2 H) 8.35 (s, 1 H) 8.53 (s, 1 H) 9.24 (br. s., 1 H).

TABLE 2

| Object ID | FLIPR EC50 (nM)/(% Antagonism) | | |
|---|---|---|---|
| | S1P$_1$ | S1P$_2$ | S1P$_3$ |
| 1 | >8300 | 47 (96) | >8300 |
| | | 2.9 (33P S1P) | |
| 2 | >8300 | 118 (91) | >8300 |
| | | 23.8 (33P S1P) | |
| 3 | >8300 | 8 (99) | >8300 |
| | | 5.7 (33P S1P) | |
| 4 | >8300 | 1.5 (33P S1P) | >8300 |
| 5 | >8300 | 135 (82) | >8300 |
| 6 | >8300 | 11 (95) | >8300 |
| | | 2.2 (33P S1P) | |
| 7 | >8300 | 196 (98) | >8300 |
| 8 | >8300 | 12 (99) | >8300 |
| | | 6.4 (33P S1P) | |
| 9 | >8300 | 149 (52) | >8300 |
| | | 26.4 (33P S1P) | |
| 10 | >8300 | 58 (98) | >8300 |
| | | 9.9 (33P S1P) | |
| 11 | >8300 | 9 (98) | >8300 |
| | | 5 (33P S1P) | |
| 12 | >8300 | 24 (99) | >8300 |
| | | 2.1 (33P S1P) | |
| 13 | >8300 | 0.5 (33P S1P) | >8300 |
| 14 | >8300 | 0.5 (33P S1P) | >8300 |
| 15 | >8300 | 0.2 (33P S1P) | >8300 |
| 16 | >8300 | 0.1 (33P S1)P | >8300 |
| 17 | >8300 | 0.1 (33P S1P) | >8300 |
| 18 | >8300 | 266 (33P S1P) | >8300 |
| 19 | >8300 | 40 (33P S1P) | >8300 |

| Example No | FLIPR EC50 (nM)/(% Antagonism) | | |
|---|---|---|---|
| | S1P$_1$ | S1P$_2$ | S1P$_3$ |
| 20 | >8300 | 196 (33P S1P) | >8300 |
| 21 | >8300 | 81 (33P S1P) | >8300 |
| 22 | >8300 | 199 (33P S1P) | >8300 |
| 23 | >8300 | 188 (33P S1P) | >8300 |
| 24 | >8300 | 390 (33P S1P) | >8300 |
| 25 | >8300 | 451 (33P S1P) | >8300 |
| 26 | >8300 | 196 (33P S1P) | >8300 |
| 27 | >8300 | 386 (33P S1P) | >8300 |

As can be seen from the above results, the pyrazolopyridinyl compounds of this invention are preferred over the benzopyridinyl or pyrido pyridinyl compounds. In particular, the pyrazolopyridinyl compounds which comprise substituted aryl which is pyridinyl are especially preferred. And finally, the pyrazolopyridinyl compounds which comprise substituted aryl which is pyridinyl and wherein the substitution pattern is o-halo, o-alkyloxy, more preferably o-chloro, o-ethyyloxy, propyloxy or butyloxy are most preferred.

As a result of the above activity of the compounds utilized in the method of the present invention, it is clear that such compounds may be used in treating and/or preventing the following diseases and conditions of the eye as well as other diseases and conditions discussed below. (It should be noted that "treating" means ameliorating and/or modulating a disease or disorder that exists in a subject (whether the subject is aware of the disease or disorder or not) or delaying the onset of the disease or disorder and "preventing" means preventing the recurrence, onset or development of one or more symptoms of a disease or disorder in a subject by administering one or more compounds of the invention.)

Ocular diseases; wet and dry age-related macular degeneration, diabetic retinopathy, retinopathy of prematurity, geographic atrophy, glaucomatous optic neuropathy Systemic vascular barrier related diseases; various inflammatory diseases, including acute lung injury, its prevention, sepsis, tumor metastasis, atherosclerosis, pulmonary edemas, and ventilation-induced lung injury Allergies and other inflammatory diseases; urticaria, bronchial asthma, and other airway inflammations including pulmonary emphysema and chronic obstructive pulmonary diseases Cardiac protection; Ischemia/reperfusion injury, atherosclerosis Anti-fibrosis; ocular, cardiac, hepatic and pulmonary fibrosis, proliferative vitreoretinopathy, cicatricial pemphigoid, surgically induced fibrosis in cornea, conjunctiva and tenon Pains and anti-inflammation; Acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains Wound Healing; scar-free healing of wounds from cosmetic skin surgery and ocular surgery, GI surgery, general surgery, various mechanical and heat injuries See, for example, the following articles:
1. Hla, Timothy "Inhibitor of the Receptor Activity of the S1P2 Receptor for Inhibiting Pathological Angiogenesis in the eye." PCT Int. Appl. (2008), 54 pp. WO 2008154470 A1
2. Athanasia Skoura, Teresa Sanchez, Kevin Claffey, Suzanne M. Mandala, Richard L. Proia, and Timothy Hla "Essential role of sphingosine 1-phosphate receptor 2 in pathological angiogenesis of the mouse retina." *J Clin Invest*. 2007 Sep. 4; 117(9): 2506-2516.
3. Serriere-Lanneau V, Teixeira-Clerc F, Li L, et al. The sphingosine 1-phosphate receptor S1P2 triggers hepatic wound healing. *FASEB J* 2007 21:2005-13.

The foregoing description details specific methods and compositions that can be employed to practice the present invention, and represents the best mode contemplated. Thus, however detailed the foregoing may appear in text, it should not be construed as limiting the overall scope hereof; rather, the ambit of the present invention was to be governed only by the lawful construction of the appended claims. In particular, the present invention includes, as preferred novel compounds, having subtype-selective modulating activity of sphingosine-1-phosphate-2 (S1P$_2$) receptors, compounds selected from the group consisting of 1-(2-chloro-6-loweralkyloxypyridin-4-yl)-3-((7-isopropyl-1,3-dimethyl-1H-pyrazolo[4,3-b]pyridin-5-yl)methyl)ureas and 1-(2-chloro-6-loweralkyloxypyridin-4-yl)-3-((7-isopropyl-1,3-dimethyl-1H-pyrazolo[4,3-b]pyridin-5-yl)imino)ureas.

What is claimed is:
1. A method of wound healing, treating wet and dry age-related macular degeneration, geographic atrophy, glaucomatous optic neuropathy, or vision threatening retinopathies associated with the sphingosine-1-phosphate 2 receptor modulation, wherein the retinopathy is selected from: diabetic retinopathy and retinopathy of prematurity, which comprises administering to a patient in need thereof, a pharmaceutical composition comprising a compound of Formula I or a pharmaceutically acceptable salt thereof:

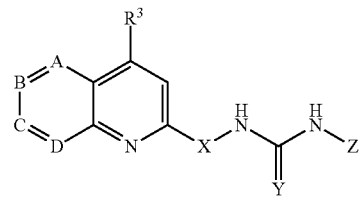

Formula I wherein:
A is a direct bond or (CR) and B, C and D are independently selected from the group consisting of (CR) and N, wherein R is H or alkyl, provided however, not all, of B, C and D are N and, when A is a direct bond, D is (CR);
R$^3$ is selected from the group consisting of alkyl;
X is selected from the group consisting of O, NR$^4$ and CR$^4$R$^5$, wherein R$^4$ and R$^5$ are independently selected from the group consisting of H and alkyl;
Y is selected from the group consisting of O or S; and
Z is a substituted aryl ring.

2. The method according to claim 1, wherein the compound is represented by the Formula II

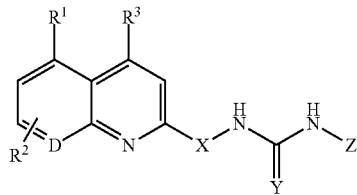

Formula II wherein:
R$^1$ and R$^2$ are independently selected from the group consisting of H and alkyl, methoxy, hydroxyl, halogen, nitrile, and trifluoromethyl;
R$^3$ is independently selected from the group consisting of alkyl, methoxy, hydroxyl, halogen, nitrile, and trifluoromethyl ;
D is CR or N;
R is H or alkyl;
X is O, NR$^4$, CR$^4$R$^5$, where R$^4$ and R$^5$ are independently selected from the group consisting of H and alkyl, e.g. lower alkyl and may have from 1 to 10 carbons, and may be cyclic or branched chain alkyl having 3 to 10 carbons, methoxy, hydroxyl, F, Br, I, nitrile, and trifluoromethyl ;
Y is O or S,
Z is a substituted aryl ring, having the following structure:

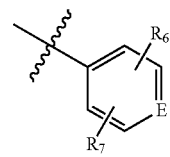

wherein R$^6$ and R$^7$ are independently selected from the group consisting of alkyl and may include from 1 to 10 carbons, and may be cyclic or branched chain alkyl having 3 to 10 carbons, methoxy, hydroxyl, halogen, nitrile, and trifluoromethyl; and E is N or CR.

3. The method according to claim 2, wherein:

$R^1$, $R^2$ and $R^3$ are independently H, halogen, methyl, or isopropyl;

X is $NR^4$;

$R^4$ is H;

Y is O;

$R^6$ and $R^7$ are independently H or chloro;

E is N or CR; and

R is H.

4. The method according to claim 2, wherein said compound is selected from the group consisting of:

N-(3,5-dichlorophenyl)-2-(4-methyl-1,8-naphthyridin-2-yl)hydrazinecarboxamide;

N-(3,5-dichlorophenyl)-2-(4-isopropyl-1,8-naphthyridin-2-yl)hydrazinecarboxamide;

N-(3,5-dichlorophenyl)-2-(4-isopropyl-5,8-dimethylquinolin-2-yl)hydrazinecarboxamide;

N-(3,5-dichlorophenyl)-2-(4-isopropylquinolin-2-yl)hydrazinecarboxamide;

N-(2,6-dichloropyridin-4-yl)-2-(4,8-dimethylquinolin-2-yl)hydrazinecarboxamide;

N-(3,5-dichlorophenyl)-2-(4,8-dimethylquinolin-2-yl)hydrazinecarboxamide;

N-(2,6-dichloropyridin-4-yl)-2-(4-methylquinolin-2-yl)hydrazinecarboxamide; and

N-(3,5-dichlorophenyl)-2-(4,5,8-trimethylquinolin-2-yl)hydrazinecarboxamide.

5. The method according to claim 1, wherein the compound is represented by the Formula III

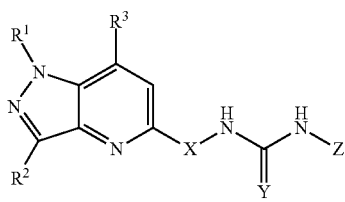

Formula III wherein:

$R^1$ $R^2$ are independently selected from the group consisting of H and alkyl, methoxy, hydroxyl, halogen, nitrile, and trifluoromethyl;

$R^3$ is independently selected from the group consisting of alkyl, methoxy, hydroxyl, halogen, nitrile, and trifluoromethyl ;

X is O, $NR^4$, $CR^4R^5$, where $R^4$ and $R^5$ are independently selected from the group consisting of H and alkyl, e.g. lower alkyl and may have from 1 to 10 carbons, and may be cyclic or branched chain alkyl having 3 to 10 carbons, methoxy, hydroxyl, F, Br, I, nitrile, and trifluoromethyl ;

Y is O or S;

R is H, methoxy or alkyl;

Z is a substituted aryl ring, having the following structure:

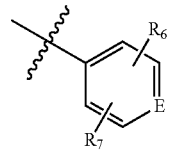

wherein $R^6$ and $R^7$ are independently selected from the group consisting of alkyl and may include from 1 to 10 carbons, and may be cyclic or branched chain alkyl having 3 to 10 carbons, methoxy, ethoxy, propoxy, butoxy, hydroxyl, halogen, nitrile, and trifluoromethyl; and E is N or CR.

6. The method according to claim 5, wherein:

$R^1$, $R^2$ and $R^3$ are independently methyl or isopropyl;

X is $NR^4$ or $CR^4R^5$;

$R^4$ is H;

$R^5$ is H;

Y is O;

$R^6$ and $R^7$ are independently selected from the group consisting of alkyl and may include from 1 to 5 carbons, methoxy, ethoxy, propoxy, butoxy, chloro and trifluoromethyl;

E is N or CR; and

R is H or methoxy.

7. The method according to claim 5, wherein compound is selected from the group consisting of:

N-(3,5-dichlorophenyl)-2-(7-isopropyl-1,3-dimethyl-1H-pyrazolo[4,3-b]pyridin-5-yl)hydrazinecarboxamide;

1-(2,6-dichloropyridin-4-yl)-3-((7-isopropyl-1,3-dimethyl-1H-pyrazolo[4,3-b]pyridin-5-yl)methyl)urea;

N-(2-butyl-6-chloropyridin-4-yl)-2-(7-isopropyl-1,3-dimethyl-1H-pyrazolo[4,3-b]pyridin-5-yl)hydrazinecarboxamide;

N-(2-chloro-6-ethoxypyridin-4-yl)-2-(7-isopropyl-1,3-dimethyl-1H-pyrazolo[4,3-b]pyridin-5-yl)hydrazinecarboxamide;

1-(3,5-dichlorophenyl)-3-((1,3,7-trimethyl-1H-pyrazolo[4,3-b]pyridin-5-yl)methyl)urea;

N-(2,6-dichloropyridin-4-yl)-2-(7-isopropyl-1,3-dimethyl-1H-pyrazolo[4,3-b]pyridin-5-yl)hydrazinecarboxamide;

N-(3,5-bis(trifluoromethyl)phenyl)-2-(7-isopropyl-1,3-dimethyl-1H-pyrazolo[4,3-b]pyridin-5-yl)hydrazinecarboxamide;

N-(3-chloro-5-methoxypyridin-4-yl)-2-(7-isopropyl-1,3-dimethyl-1H-pyrazolo[4,3-b]pyridin-5-yl)hydrazinecarboxamide;

1-(2,6-dichlorophenyl)-3-((7-isopropyl-1,3-dimethyl-1H-pyrazolo[4,3-b]pyridin-5-yl)methyl)urea;

1-(2-chloro-6-methoxypyridin-4-yl)-3-((7-isopropyl-1,3-dimethyl-1H-pyrazolo[4,3-b]pyridin-5-yl)methyl)urea;

N-(2-chloro-6-propylpyridin-4-yl)-2-(7-isopropyl-1,3-dimethyl-1H-pyrazolo[4,3-b]pyridin-5-yl)hydrazinecarboxamide;

1-(2-chloro-6-propylpyridin-4-yl)-3-((7-isopropyl-1,3-dimethyl-1H-pyrazolo[4,3-b]pyridin-5-yl)methyl)urea;

1-(2-chloro-6-ethoxypyridin-4-yl)-3-((7-isopropyl-1,3-dimethyl-1H-pyrazolo[4,3-b]pyridin-5-yl)methyl)urea;

1-(2-chloro-6-propoxypyridin-4-yl)-3-((7-isopropyl-1,3-dimethyl-1H-pyrazolo[4,3-b]pyridin-5-yl)methyl)urea;

N-(2-chloro-6-propoxypyridin-4-yl)-2-(7-isopropyl-1,3-dimethyl-1H-pyrazolo[4,3-b]pyridin-5-yl)hydrazinecarboxamide;

N-(2-butoxy-6-chloropyridin-4-yl)-2-(7-isopropyl-1,3-dimethyl-1H-pyrazolo[4,3-b]pyridin-5-yl)hydrazinecarboxamide;

1-(2-butoxy-6-chloropyridin-4-yl)-3-((7-isopropyl-1,3-dimethyl-1H-pyrazolo[4,3-b]pyridin-5-yl)methyl)urea;

N-(2-ethoxypyridin-4-yl)-2-(7-isopropyl-1,3-dimethyl-1H-pyrazolo[4,3-b]pyridin-5-yl)hydrazinecarboxamide; and N-(5-chloro-2,4-dimethoxyphenyl)-2-(7-isopropyl-1,3-dimethyl-1H-pyrazolo[4,3-b]pyridin-5-yl)hydrazinecarboxamide.

8. The method according to claim 1, wherein the method is for wound healing.

9. The method according to claim 1, wherein the method is for treating diabetic retinopathy.

10. The method according to claim 1, wherein the method is for treating retinopathy of prematurity.

11. The method according to claim 1, wherein the method is for treating wet and dry age-related macular degeneration.

12. The method according to claim 1, wherein the method is for treating geographic atrophy.

* * * * *

UNITED STATES PATENT AND TRADEMARK OFFICE
CERTIFICATE OF CORRECTION

PATENT NO. : 8,703,797 B2
APPLICATION NO. : 13/929451
DATED : April 22, 2014
INVENTOR(S) : Wenkui K. Fang et al.

It is certified that error appears in the above-identified patent and that said Letters Patent is hereby corrected as shown below:

On the Title Page

Item (56), under "Other Publications", in column 2, lines 1-2, delete "Sphingosine 1-Phosphate" and insert -- Sphingosine-1-Phosphate --, therefor.

Item (56), under "Other Publications", in column 2, line 8, delete "Sphingosine 1-Phosphate" and insert -- Sphingosine-1-Phosphate --, therefor.

Item (56), under "Other Publications", in column 2, line 12, delete "sphingosine 1-phosphate" and insert -- sphingosine-1-phosphate --, therefor.

Item (56), under "Other Publications", in column 2, lines 22-23, delete "sphingosine 1—phosphate" and insert -- sphingosine-1-phosphate --, therefor.

Item (56), under "Other Publications", in column 2, line 23, delete "angiogensis" and insert -- angiogenesis --, therefor.

Item (57), under "Abstract", in column 2, line 3, delete "and or" and insert -- and/or --, therefor.

On page 2, in column 1, Item (56) under "Other Publications , lines 1-2, delete "Sphingosine 1-Phosphate" and insert -- Sphingosine-1-Phosphate --, therefor.

On page 2, in column 2, Item (56) under "Other Publications", line 1, delete "sphingosine 1-phosphate" and insert -- sphingosine-1-phosphate --, therefor.

On page 2, in column 2, Item (56) under "Other Publications", line 4, delete "Mehrotram" and insert -- Mehrotra --, therefor.

On page 2, in column 2, Item (56) under "Other Publications", line 6, delete "Heterocylcic" and insert -- Heterocyclic --, therefor.

In the Specification

In column 1, line 57, delete "sphingomeyeline" and insert -- sphingomyelin --, therefor.

Signed and Sealed this
Seventh Day of October, 2014

Michelle K. Lee
*Deputy Director of the United States Patent and Trademark Office*

CERTIFICATE OF CORRECTION (continued)
U.S. Pat. No. 8,703,797 B2

In column 1, line 60, delete "spingosine" and insert -- sphingosine --, therefor.

In column 2, line 15, delete "spingosine" and insert -- sphingosine --, therefor.

In column 2, line 24, delete "Sphingosine-1 phosphate" and insert -- Sphingosine-1-phosphate --, therefor.

In column 3, line 1, delete "spingosine" and insert -- sphingosine --, therefor.

In column 3, line 3, delete "spingosine" and insert -- sphingosine --, therefor.

In column 3, line 15, delete "and or" and insert -- and/or --, therefor.

In column 4, line 28, delete "N" and insert -- N. --, therefor.

In column 6, line 14, delete "sphingosine 1-phosphate" and insert -- sphingosine-1-phosphate --, therefor.

In column 6, line 17, delete "sphingosine 1-phosphate." and insert -- sphingosine-1-phosphate. --, therefor.

In column 6, line 18, delete "sphingosine 1-phosphate," and insert -- sphingosine-1-phosphate, --, therefor.

In column 6, line 27, delete "tenon" and insert -- tenon. --, therefor.

In column 15, line 56, delete "dichloromethane" and insert -- dichloromethane. --, therefor.

In column 15, line 57, delete "tetrahydrofuran" and insert -- tetrahydrofuran. --, therefor.

In column 15, line 58, delete "ethylacetate" and insert -- ethylacetate. --, therefor.

In column 17, line 41, delete "R'" and insert -- R''' --, therefor.

In column 17, line 48, delete "—$S(O)_2$—R"," and insert -- —$S(O)_2$— R"", --, therefor.

In column 17, line 49, delete "alkyaryl," and insert -- alkylaryl, --, therefor.

In column 21, line 34, delete "procure" and insert -- procedure --, therefor.

In column 21, line 38, delete "1H)," and insert -- 1 H), --, therefor.

In column 23, line 32, delete "[4,3-h]" and insert -- [4,3-b] --, therefor.

In column 24, line 18, delete "[4,3-h]" and insert -- [4,3-b] --, therefor.

In column 24, line 59, delete "2.6-dichloropyridine" and insert -- 2,6-dichloropyridine --, therefor.

In column 24, line 62, delete "ppm" and insert -- δ ppm --, therefor.

In column 25, line 5, delete "[4,3-h]" and insert -- [4,3-b] --, therefor.

In column 25, line 50, delete "1H))." and insert -- 1 H). --, therefor.

In column 28, line 40, delete "[4,3-h]" and insert -- [4,3-b] --, therefor.

In column 30, line 31, delete "[4,3-h]" and insert -- [4,3-b] --, therefor.

In column 31, line 8, delete "[4,3-h]" and insert -- [4,3-b] --, therefor.

In column 31, line 56, delete "[4,3-h]" and insert -- [4,3-b] --, therefor.

In column 35, line 41, delete "(lx" and insert -- (1× --, therefor.

In column 35, line 59, delete "(lx" and insert -- (1× --, therefor.

In column 36, line 10, delete "naphthyridine" and insert -- naphthyridine: --, therefor.

In column 36, line 28, delete "(lx" and insert -- (1× --, therefor.

In column 37, line 42, delete "1H)" and insert -- 1 H) --, therefor.

In column 39, line 12, delete "(lx" and insert -- (1× --, therefor.

In column 43, line 46, delete "(lx" and insert -- (1× --, therefor.

In column 44, line 28 (Table 2), delete "S1)P" and insert -- S1P) --, therefor.

In column 44, line 58, delete "ethyyloxy," and insert -- ethyloxy, --, therefor.

In column 45, line 33, delete "A1" and insert -- A1. --, therefor.

In column 45, line 36, delete "sphingosine 1-phosphate" and insert -- sphingosine-1-phosphate --, therefor.

In column 45, line 40, delete "sphingosine 1-phosphate" and insert -- sphingosine-1-phosphate --, therefor.

In the Claims

In column 46, lines 42-43, in claim 2, delete "trifluoromethyl ;" and insert -- trifluoromethyl; --, therefor.

In column 46, lines 51-52, in claim 2, delete "trifluoromethyl ;" and insert -- trifluoromethyl; --, therefor.

In column 47, line 51, in claim 5, delete "$R^1$ $R^2$" and insert -- $R^1$ and $R^2$ --, therefor.

In column 47, lines 55-56, in claim 5, delete "trifluoromethyl ;" and insert -- trifluoromethyl; --, therefor.

In column 47, lines 61-62, in claim 5, delete "trifluoromethyl ;" and insert -- trifluoromethyl; --, therefor.

In column 48, line 15, in claim 5, delete "Nor" and insert -- N or --, therefor.